United States Patent
Chen et al.

(10) Patent No.: US 11,802,879 B2
(45) Date of Patent: Oct. 31, 2023

(54) IDENTIFICATION AND QUANTIFICATION OF CONJUGATED PEPTIDES IN ANTIBODY DRUG CONJUGATES BY MASS SPECTROMETRY

(71) Applicant: Waters Technologies Corporation, Milford, MA (US)

(72) Inventors: Liuxi Chen, Saratoga, CA (US); Weibin Chen, Holliston, MA (US); Steven Cubbedge, Auburn, MA (US)

(73) Assignee: Waters Technologies Corporation, Milford, MA (US)

( * ) Notice: Subject to any disclaimer, the term of this patent is extended or adjusted under 35 U.S.C. 154(b) by 715 days.

(21) Appl. No.: 16/080,903

(22) PCT Filed: Mar. 2, 2017

(86) PCT No.: PCT/US2017/020410
§ 371 (c)(1),
(2) Date: Aug. 29, 2018

(87) PCT Pub. No.: WO2017/151892
PCT Pub. Date: Sep. 8, 2017

(65) Prior Publication Data
US 2019/0041394 A1 Feb. 7, 2019

Related U.S. Application Data

(60) Provisional application No. 62/302,333, filed on Mar. 2, 2016.

(51) Int. Cl.
*G01N 33/68* (2006.01)
*G01N 30/72* (2006.01)
(Continued)

(52) U.S. Cl.
CPC ........ *G01N 33/6848* (2013.01); *G01N 30/72* (2013.01); *G01N 30/7233* (2013.01); *G01N 2030/027* (2013.01); *H01J 49/004* (2013.01)

(58) Field of Classification Search
USPC .......................................................... 436/173
See application file for complete search history.

(56) References Cited

U.S. PATENT DOCUMENTS

| 4,243,749 A | 1/1981 | Sadeh et al. |
| 2005/0232929 A1 | 10/2005 | Kadkhodayan et al. |

(Continued)

FOREIGN PATENT DOCUMENTS

| CN | 104160274 A | 11/2014 |
| WO | 2015/162563 A1 | 10/2015 |
| WO | 2015/191980 A1 | 12/2015 |

OTHER PUBLICATIONS

Doneanu, C. et al. Optimization of Trypsin Digestion for MRM Quantification of Therapeutic Proteins in Serum, Waters Corporation, 2012 (Year: 2012).*

(Continued)

*Primary Examiner* — Xiaoyun R Xu
(74) *Attorney, Agent, or Firm* — WOMBLE BOND DICKINSON (US) LLP; Deborah M. Vernon; Dennis J. Parad

(57) ABSTRACT

The present disclosure relates to a streamlined, complete workflow for the qualitative and the quantitative analysis of conjugated peptides from antibody-drug conjugate (ADC) compounds.

12 Claims, 10 Drawing Sheets

Specification includes a Sequence Listing.

(51) Int. Cl.
*H01J 49/00* (2006.01)
*G01N 30/02* (2006.01)

(56) References Cited

U.S. PATENT DOCUMENTS

| | | |
|---|---|---|
| 2009/0286258 A1 | 11/2009 | Kaur et al. |
| 2011/0312010 A1 | 12/2011 | Manuilov et al. |
| 2012/0245857 A1 | 9/2012 | Lee et al. |
| 2014/0242624 A1 | 8/2014 | Valliere-Douglass et al. |

OTHER PUBLICATIONS

Wakankar, A. et al. Analytical methods for physicochemical characterization of antibody drug conjugates, Landes Bioscience, 3(2), 161-172. (Year: 2011).*
Basa. "Drug-to-Antibody Ratio (DAR) and Drug Load Distribution by LC-ESI-MS." Antibody-Drug Conjugates. 1045 (2013): 285-293.
Chen et al. "In-depth structural characterization of Kadcyla® (ado-trastuzumab emtansine) and its biosimilar candidate." mAbs. 8.7(2016): 1210-1223.
Marcoux et al. "Native mass spectrometry and ion mobility characterization of trastuzumab emtansine, a lysine-linked antibody drug conjugate." Protein Sci. 24(2015): 1210-1223.
Ni et al. "Complete Mapping of a Cystine Knot and Nested Disulfides of Recombinant Human Arylsulfatase A by Multi-Enzyme Digestion and LC-MS Analaysis Using CID and ETD." J. Am. Soc. Mass Spectrom. 24(2013): 125-133.
Search Report issued in European Application No. 17760797.5 dated Aug. 29, 2019.
Duddu, S. P. "Effect of glass transition temperature on the stability of lyophilized formulations containing a chimeric therapeutic monoclonal antibody." Pharm Res 1997, 14 (5), 591-5.
Ejima, D. et al., "Effects of acid exposure on the conformation, stability, and aggregation of monoclonal antibodies." Proteins 2007, 66 (4), 954-62.
Ionescu, R. et al., Contribution of variable domains to the stability of humanized IgG1 monoclonal antibodies. Journal of Pharmaceutical Sciences 2008, 97 (4), 1414-1426.
Jung, S. K. et al., "Physicochemical characterization of Remsima." mAbs 2014, 6 (5), 1163-1177.
Kim, M. T. et al., "Statistical modeling of the drug load distribution on trastuzumab emtansine (Kadcyla), a lysine-linked antibody drug conjugate." Bioconjugate Chemistry 2014, 25 (7), 1223-1232.
Lambert, J. M., "Drug-conjugated monoclonal antibodies for the treatment of cancer," Current Opinion in Pharmacology 2005, 5 (5), 543-549.
Lazar, A. C.; et al., "Analysis of the composition of immunoconjugates using size-exclusion chromatography coupled to mass spectrometry." Rapid Communications in Mass Spectrometry 2005, 19 (13), 1806-1814.
Leavell, M. D. et al., "Strategy for selective chemical cross-linking of tyrosine and lysine residues." J Am Soc Mass Spectrom 2004, 15(11), 1604-11.
Liu, H. et al. "Effect of posttranslational modifications on the thermal stability of a recombinant monoclonal antibody." Immunol Lett 2006, 106 (2), 144-53.
Phillips, G. D.; et al., "Targeting HER2-positive breast cancer with trastuzumab-DM1, an antibody-cytotoxic drug conjugate." Cancer Research 2008, 68 (22), 9280-9290.
Strop, P. et al., "Location Matters: Site of Conjugation Modulates Stability and Pharmacokinetics of Antibody Drug Conjugates." Chemistry & Biology 2013, 20 (2), 161-167.
Wakankar, A. A. et al., "Physicochemical Stability of the Antibody-Drug Conjugate Trastuzumab-DM1: Changes due to Modification and Conjugation Processes." Bioconjugate Chemistry 2010, 21(9), 1588-1595.
Wang, L. et al, "Structural characterization of the maytansinoid-monoclonal antibody immunoconjugate, huN901-DM1, by mass spectrometry." Protein Science: A Publication of the Protein Society 2005, 14 (9), 2436-2446.
Weiner, L. M., "Building better magic bullets—improving unconjugated monoclonal antibody therapy for cancer," Nature Reviews Cancer 2007, 7 (9), 701-706.
Xie, H. et al., "Rapid comparison of a candidate biosimilar to an innovator monoclonal antibody with advanced liquid chromatography and mass spectrometry technologies" MAbs 2010, 2 (4), 379-94.
Zhang, Z., "Large-scale identification and quantification of covalent modifications in therapeutic proteins." Analytical Chemistry 2009, 81 (20), 8354-8364.
Chen et al. "Automated Quantitative Analysis of Antibody Drug Conjugates Using an Accurate Mass Screening Workflow in the UNIFI Scientific Information System." Waters Application Note Feb. 29, 2016.
Chen et al. "Profiling, Localizing and Quantifying Conjugation Sites of Lysine-Conjugated ADCs." Waters Poster. Dec. 31, 2015.
International Search Report and the Written Opinion from Corresponding PCT/US2017/020410; Completed on Aug. 9, 2017; dated Aug. 25, 2017.

* cited by examiner

Figure 11

| Name | Run | ADC | | |
|---|---|---|---|---|
| | | Purity (%) | X±S | CV (%) |
| Innovator ADC | 1 | 1.19 | 1.15±0.05 | 4.49 |
| | 2 | 1.18 | | |
| | 3 | 1.09 | | |
| Biosimilar ADC | 1 | 1.36 | 1.33±0.06 | 4.46 |
| | 2 | 1.36 | | |
| | 3 | 1.26 | | |

IDENTIFICATION AND QUANTIFICATION OF CONJUGATED PEPTIDES IN ANTIBODY DRUG CONJUGATES BY MASS SPECTROMETRY

CROSS-REFERENCE TO RELATED APPLICATIONS

This application is a National Stage Application of International Application No. PCT/US2017/020410, filed Mar. 2, 2017, which claims the benefit of and priority to U.S. Provisional Application No. 62/302,333, filed Mar. 2, 2016, and entitled "IDENTIFICATION AND QUANTIFICATION OF CONJUGATED PEPTIDES IN ANTIBODY DRUG CONJUGATES BY MASS SPECTROMETRY." Each of the foregoing applications is incorporated herein by reference in its entirety.

FIELD OF THE INVENTION

The present disclosure relates to a streamlined, complete workflow for the qualitative and the quantitative analysis of conjugated peptides from antibody-drug conjugate (ADC) compounds.

BACKGROUND

Antibody-drug conjugate (ADC) compounds represent a growing class of immunoconjugate therapies. ADC compounds are complex molecules composed of a monoclonal antibody connected to a biologically active, highly cytotoxic drug via a cleavable (e.g., acid labile linkers, protease cleavable linkers, and disulfide linkers) or a non-cleavable linker. The conjugation of potent drugs to a monoclonal antibody enables the targeted delivery of toxic payloads to tumor surfaces while minimizing systemic toxicity effects to healthy tissue, thus improving the therapeutic window for such modalities in the treatment of cancer.

Incomplete conjugation processes can result in free or non-conjugated drug, drug-linker, or drug related impurities. Additionally, degradation products can occur over time in formulation as well as in vivo. Accordingly, both structural characterization and qualitative analysis of ADCs prove challenging.

Traditionally, quantification of conjugated peptides and site occupancy ratio determination has been accomplished using UV methods. The drawbacks for UV quantification include low sensitivity, insufficient selectivity and relative long analysis time. MS-based quantification can provide higher selectivity and sensitivity compared to UV based methods. However, to-date the biopharmaceutical industry lacks a complete workflow that enables efficient identification and quantification of ADC peptides.

SUMMARY OF THE INVENTION

The present disclosure relates to a streamlined, complete workflow for the qualitative and the quantitative analysis of conjugated peptides from antibody-drug conjugate (ADC) compounds.

Accordingly, provided herein are methods for analyzing site occupancy ratios in antibody-drug conjugates. One embodiment of the method comprises two steps. One step involves ionizing a sample comprising an antibody-drug conjugate compound and a peptide. Ionization serves to form radical ion fragments of the antibody-drug conjugate compound and of the peptide. Another step involves detecting the mass-to-charge ratios associated with the radical ion fragments.

Another embodiment of the method comprises at least three steps. One step involves providing a sample comprising an antibody-drug conjugate compound and a peptide. Another step involves exposing the sample to de-salting. Another step involves exposing the sample to multi-enzyme digestion. Then the sample comprising an antibody-drug conjugate compound and a peptide is ionized. Ionization serves to form radical ion fragments of the antibody-drug conjugate compound and of the peptide. Subsequently, the mass-to-charge ratios associated with the radical ion fragments are detected.

Still another embodiment of the method comprises three steps. One step involves ionizing a sample comprising an antibody-drug conjugate compound and a peptide. Ionization serves to form radical ion fragments of the antibody-drug conjugate compound and of the peptide. Another step involves; detecting the mass-to-charge ratios associated with the radical ion fragments. Another step involves selecting two separate groups of mass-to-charge ratios of the radical ion fragments. The first group of mass-to-charge ratios may be associated with the radical ion fragments of the conjugated peptide. The second group of mass-to-charge ratios may be associated with the radical ion fragments of the unconjugated peptide.

Yet another embodiment of the method includes three steps. One step involves ionizing a sample comprising an antibody-drug conjugate compound and a peptide. Ionization serves to form radical ion fragments of the antibody-drug conjugate compound and of the peptide. Another step involves detecting the mass-to-charge ratios associated with the radical ion fragments. Another step involves monitoring two separate groups of mass-to-charge ratios of the radical ion fragments. The first group of mass-to-charge ratios may be associated with the radical ion fragments of the conjugated peptide. The second group of mass-to-charge ratios may be associated with the radical ion fragments of the unconjugated peptide.

The methods provided herein enable the analysis of the mass-to-charge ratios of the radical ion fragments to determine the site occupancy ratio of occupied to unoccupied sites in the antibody-drug conjugate compound.

The above embodiments of the methods provided herein possess one or more of the following advantages. For example, certain embodiments provide a streamlined workflow that eliminates complicated steps for identification and quantification of ADC peptides. Certain other embodiments offer higher selectivity and sensitivity then previous workflows.

BRIEF DESCRIPTION OF THE DRAWINGS

FIG. 11 shows the free drug contents of the ADC samples.

DETAILED DESCRIPTION OF THE INVENTION

Figure 1:
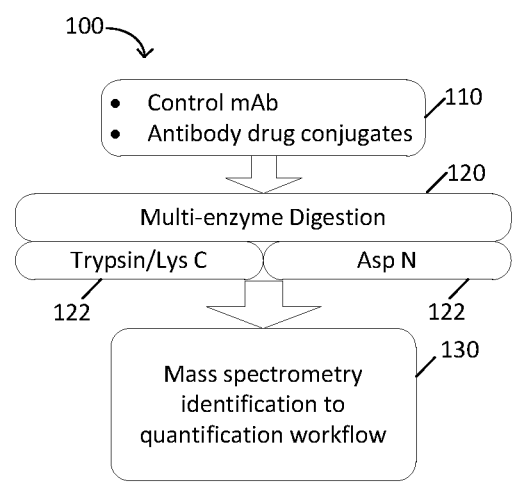
FIG. 1 is a schematic showing one embodiment the method of the invention.

Reference will now be made in detail to certain embodiments of the invention, examples of which are illustrated in the accompanying figures. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described.

Definitions

Unless stated otherwise, the following terms and phrases as used herein are intended to have the following meanings:

As used herein "antibody drug conjugates: or "ADCs" are monoclonal antibodies (mAbs) attached to biologically active drugs by chemical linkers with labile bonds.

"Antibody" is used herein in the broadest sense and specifically covers monoclonal antibodies, polyclonal antibodies, multispecific antibodies (e.g., bispecific antibodies), and antibody fragments. Antibodies may be murine, human, humanized, chimeric, or derived from other species. An antibody is a protein generated by the immune system that is capable of recognizing and binding to a specific antigen.

(Janeway, et al (2001) "Immunobiology", 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody.

Antibody also refers to a full-length immunoglobulin molecule or an immunologically active portion of a full-length immunoglobulin molecule, i.e., a molecule that contains an antigen binding site that immuno specifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

The term "linker unit" refers to the direct or indirect linkage of the antibody to the drug. Attachment of a linker to a mAb can be accomplished in a variety of ways, such as through surface lysines, reductive-coupling to oxidized carbohydrates, and through cysteine residues liberated by reducing interchain disulfide linkages. A variety of ADC linkage systems are known in the art, including hydrazone-, disulfide- and peptide-based linkages.

A "drug" is any substance having biological or detectable activity, for example, therapeutic agents, detectable labels, binding agents, etc., and prodrugs, which are metabolized to an active agent in vivo. The terms drug and payload are used interchangeably.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrometric instrument where, due to a combination of magnetic and electric fields, the ions follow a path in space that is dependent upon mass ("m") and charge ("z").

As used herein the term "MS$^E$" refers to a method for tandem mass spectrometry data acquisition using alternating low-energy collision-induced dissociation and high-energy collision-induced dissociation where the former is used to obtain precursor ion accurate mass and intensity data for quantification and the latter is used to obtain product ion accurate mass.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), ultra-high performance liquid chromatography (UPLC or UHPLC), turbulent flow liquid chromatography (TFLC) (sometimes known as high turbulence liquid chromatography (HTLC) or high throughput liquid chromatography).

As used herein, the term "high performance liquid chromatography" or "HPLC" (also sometimes known as "high pressure liquid chromatography") refers to liquid chromatography in which the degree of separation is increased by forcing the mobile phase under pressure through a stationary phase, typically a densely packed column. As used herein, the term "ultra high performance liquid chromatography" or "UPLC" or "UHPLC" (sometimes known as "ultra high pressure liquid chromatography") refers to HPLC that occurs at much higher pressures than traditional HPLC techniques.

The term "LC/MS" refers to a liquid chromatograph (LC) interfaced to a mass spectrometer.

As used herein "HER2-positive breast cancer" refers to a breast cancer that tests positive for a protein called human epidermal growth factor receptor 2 (HER2), which promotes the growth of cancer cells. In about 1 of every 5 breast cancers, the cancer cells have a gene mutation that makes an excess of the HER2 protein.

The term "Human Epidermal growth factor Receptor 2" or "HER2" (also known as HER2/neu and ErbB-2) is intended to include variants, isoforms and species homologs of HER2. Preferably, binding of an antibody of the invention to HER2 inhibits the growth of cells expressing HER2 (i.e., typically tumor cells) by inhibiting formation of heteromeric complexes between HER2 and other ErbB family members, e.g., heterodimerization with EGFR or HER3.

Methods of the Invention

The present disclosure provides methods that enable a streamlined, complete a workflow for the qualitative and the quantitative analysis of conjugated peptides from ADCs. The method enables the comprehensive conjugation site identification and provides site occupancy comparison among samples or between individual conjugation sites.

An embodiment of the method of the invention is shown in FIG. 1. Therein, the disclosed workflow 100 is used for ADC peptide quantifications, and combines multi-enzyme digestion, $MS^E$ and data dependent acquisition (DDA) data acquisition, mass spectrometry identification (peptide mapping workflow), scientific library, and mass spectrometry quantification (accurate mass screening workflow).

Figure 2:
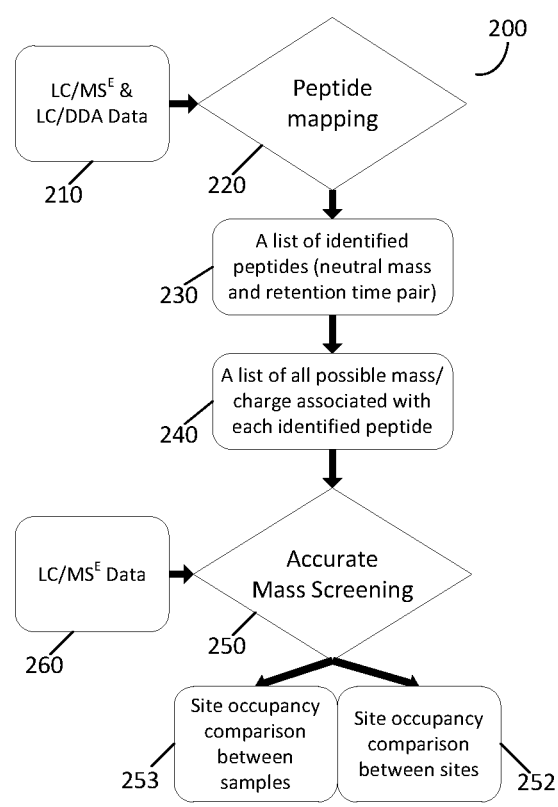
FIG. 2 is a schematic showing an alternative embodiment the method of the invention.

An alternative embodiment of the method of the invention is shown in FIG. 2. The detailed workflow 200 exemplifies the mass spectrometric identification steps of the method to the steps of the method involving mass spectrometric quantification of the ADC peptides.

$MS^E$ and DDA data acquisition by UPLC-QTOF instruments were accomplished in parallel, using the same UPLC separation gradient. Mass spectrometric identification is made through the developed algorithm, which uses the precursor ion mass matches and fragment ions matches as a means of peptide ID. The algorithm process $MS^E$, together with DDA data, to find the conjugated peptides and to confirm the individual conjugation site. Through the process, a list of identified peptides, either with or without conjugated drug, is acquired, each associating with neutral mass of the peptides and the corresponding retention time. The information is stored in a scientific library, through which a new list of all possible mass/charge associated with the peptide, i.e., multiple protonated ions, metal adduct, and insource fragment ions is generated. The algorithm subsequently uses the accurate retention time and the saved list of mass/charge to identify all the MS peaks that are associated to the unconjugated peptide and the conjugated peptide to obtain quantitative measurement (peak areas) of the peptides. All peak areas that belong to an identified peptide sequence are then combined and treated as the quantitative measure of the peptide of interest. The individual site occupancy of conjugated peptides is determined by ratio of the total peak areas of conjugated peptides (including all signal associated to the conjugated peptides) and the total peak area of all MS peak that belongs to a peptide (conjugated and unconjugated).

The methods of the instant invention address the challenges in the biopharmaceutical industry in determining site occupancy for antibody drug conjugates. The current practice to obtain site occupancy of antibody drug conjugates normally bases on ultraviolet (UV) measurement. The conjugation levels at each site were quantified by determining the decrease in the UV peak area of the unconjugated peptides (at one wavelength) and the increase of the UV peak area of the corresponding conjugated peptides (at a different wavelength with which the drug has higher absorbance) between naked antibody and conjugated antibody samples. The drawbacks for UV quantification include low sensitivity, insufficient selectivity and relative long analysis time. To obtain accurate measurement of the UV response of the peptides, each of the components needs to be chromatographically resolved to its homogeneity. Co-eluting peaks introduce error in quantifications.

The present methods utilize mass spectrometric response as a means to quantify the abundance of the peptides, which is generally two-to-three orders of magnitude more sensitive than UV response. In addition, the instant workflow identifies the targeted components first, and quantifies the related components in a separate step. The peak areas used for quantification are obtained using extracted ion chromatograms.

Accordingly, workflow 100 exemplifies one embodiment of the disclosed method. In one embodiment of workflow 100, a sample comprising an antibody-drug conjugate compound and a peptide is ionized in step 130. This ionization process serves to form radical ion fragments of the antibody-drug conjugate compound and of the peptide. Further, the mass-to-charge ratios associated with the radical ion fragments are detected.

In another embodiment of workflow 100, a sample comprising an antibody-drug conjugate compound and a peptide is provided in step 110. The sample is exposed to multienzyme digestion in step 120. Step 120 may further comprise a de-salting step. Then, the sample comprising an antibody-drug conjugate compound and a peptide is ionized in step 130. This ionization process serves to form radical ion fragments of the antibody-drug conjugate compound and of the peptide. Further, the mass-to-charge ratios associated with the radical ion fragments are detected.

Workflow 200 exemplifies an alternative embodiment of the disclosed method. Workflow 200 can include some or all of the steps of workflow 100. For example, a sample comprising an antibody-drug conjugate compound and a peptide is ionized in step 130. This ionization process serves to form radical ion fragments of the antibody-drug conjugate compound and of the peptide. Further, the mass-to-charge ratios associated with the radical ion fragments are detected and gathered in step 220. Then, two separate groups of mass-to-charge ratios of the radical ion fragments are selected in step 210. The first group of mass-to-charge ratios may be associated with the radical ion fragments of the conjugated peptide. The second group of mass-to-charge ratios is associated with the radical ion fragments of the unconjugated peptide.

In another embodiment of workflow 200, a sample comprising an antibody-drug conjugate compound and a peptide is ionized in step 130. This ionization process serves to form radical ion fragments of the antibody-drug conjugate compound and of the peptide. Subsequently, the mass-to-charge ratios associated with the radical ion fragments are detected and gathered in step 210. Then the two separate groups of mass-to-charge ratios of the radical ion fragments are monitored in step 220. The first group of mass-to-charge ratios may be associated with the radical ion fragments of the conjugated peptide. The second group of mass-to-charge ratios is associated with the radical ion fragments of the unconjugated peptide.

The methods provided herein enable the analysis of the mass-to-charge ratios of the radical ion fragments to determine the site occupancy ratio of occupied to unoccupied sites in the antibody-drug conjugate compound, e.g., steps 252 and 253 of workflow 200.

Some embodiments of the disclosed methods further comprise step 230, which comprises identifying the peptide in the sample. Alternatively, the disclosed methods may further comprise step 250, which comprises quantifying the peptide in the sample. In certain embodiments, the sample comprises conjugated and unconjugated peptide.

Some embodiments of the disclosed methods further comprise selecting two separate groups of mass-to-charge ratios of the radical ion fragments. In certain embodiments, the first group of mass-to-charge ratios is associated with the radical ion fragments of the conjugated peptide. In other embodiments, the second group of mass-to-charge ratios is associated with the radical ion fragments of the unconjugated peptide. In specific embodiments, the selection of the two separate groups of mass-to-charge ratios is based on known ion fragmentation patterns. Optionally, the known ion fragmentation patterns can be stored in a library, step 260.

In some embodiments, the methods further comprise the step of quantifying the site occupancy ratio in the sample by determining the ratio of conjugated peptide to unconjugated peptide. In other embodiments, the methods further comprise quantifying the site occupancy ratio of a single site between different samples, step 252. Still other embodiments, the methods further comprise quantifying the site occupancy ratio of one or more sites within the same sample, step 253.

Some of the disclosed methods utilize two enzymes for sample preparation, one of which cleaves at the site of conjugation and another one cleaves at the non-conjugation site (step 120). In some embodiments, multienzyme digestions include trypsin/lysC and AspN digest protein samples separately (step 122). In one embodiment, the ratio of the trypsin/Lys C to sample is about 1:100. In another embodiment, the ratio of Asp N to sample is about 1:25 (w/w). Multi-enzyme digestion offers several advantages to the instant method. First, multi-enzyme digestion facilitates maximum coverage of conjugation sites. Multi-enzyme digestion also allows for increased the confidence of the assignment given that the identified conjugation sites from both enzymes can be compared. Lastly, multi-enzyme digestion enables site occupancy comparison between samples from trypsin/LysC datasets, and site-to-site comparison within the antibody from AspN data.

It should be noted that the multi-enzyme digestion discussed herein is merely exemplary, and alternative enzymes, combinations of enzymes, and ratios thereof can be used. As such, the invented workflow can be used to identify and quantify amino acid modifications that are commonly seen in protein chemistry.

EXEMPLIFICATION

Introduction

Antibody drug conjugates (ADCs) or immunoconjugates are a sub-class of biotherapeutics that are designed to facilitate the targeted delivery of potent cytotoxic drugs to the sites of cancer cells. The creation of ADC molecules as therapeutic modality realized, to a certain degree, an ancient dream for a "magic bullet" that a targeting agent could be harnessed to deliver cytotoxic therapy directly to the source of disease.[1] ADCs are comprised of a cytotoxic drug linked to a monoclonal antibody (mAb) via a chemical linker. The combination takes advantages of the enhanced selectivity of mAbs targeting cancer-specific antigens to improve the drug delivery effect, and in the meantime utilizes some of the highly potent cell-killing agents that are otherwise too toxic to develop as therapeutics by minimizing systemic toxicity. ADCs have recently shown promise in the treatment of various cancers.[2,3] As a matter of fact, many novel ADCs are currently in preclinical, early clinical or late-stage clinical development for the treatment of solid and hematologic tumors. Two ADC drugs were recently approved recently by the US Food and Drug Administration (FDA), brentuximab vedotin (Trade name: Adcetris, Seattle Genetics), and ado-trastuzumab emtansine (T-DM1, Trade name: Kadcyla, Genentech). The commercial success of ADCs has renewed interest in the development of novel and biosimilar ADCs across the biopharmaceutical industry.

Depending on conjugation chemistry, different types of ADCs can be constructed, such as cysteine conjugated, lysine conjugated or site-specific ADCs. It is important to note that the degree of heterogeneity of the ADC varies with the strategy used for conjugating the linker drug to the antibody. At a molecular level, all ADC molecules bear complex chemical structures, combining the molecular characteristics of small-molecule drugs as well as those of large molecule mAbs. In addition, the conjugation reaction employed for the synthesis of ADCs increases the complexity of the ADC samples to a higher level by producing a mixture of ADC molecules that are heterogeneous in two regards: first, the product population contains conjugates in a range of different drug-to-antibody ratios (DARs). For example, with conjugation at lysine residues, a distribution of DARs ranging from 0 to 7 drugs has been reported.[4] Second, any two conjugates with the same DAR are likely regioisomers because the conjugation reaction is a random process and there are many surface-accessible lysine residues (as well as the N termini of the light and heavy chains) in the mAb as potential candidates for modification. For example, one study found a lysine conjugated ADC sample with DARs ranging from 0 to 6 potentially contains over 4.5 million unique molecules [*Protein Science: A Publication of the Protein Society.* 2005; 14(9):2436-2446]. Partial modification at those accessible lysine residues results in a population of products differing in conjugation sites. In contrast, the heterogeneity for cysteine-conjugated ADC samples is significantly less as there are only up to eight cysteine conjugation sites available. Consequently, the physical/chemical property varies with the degree of heterogeneity of the ADC, which determines the analysis strategy used for characterizing ADC and ensuring the product quality of ADC.

Given the outcome of conventional ADC manufacturing methods, the clinically approved ADCs had to be developed and administered as heterogeneous mixtures. This heterogeneity presents challenges to both the analysis of ADC structures, product quality and manufacturing consistency. To gain an in-depth understanding of ADC structures and product quality, therefore establishing a better quality control on the final drug product, various analytical techniques have been developed. For example, liquid chromatography-mass spectrometry (LC-MS) approaches deployed to study ADCs at the intact protein level [*Protein Science.* 2015; 24(8):1210-1223, 2: J Am Soc Mass Spectrom. 2015 October; 26(10):1791-4], the subdomain level [*MAbs.* 2015; 7(6):1036-1044], and the individual peptide level [*Protein Science* 2005; 14(9):2436-2446] are widely reported in the literature. Although these analytical techniques are the same as for other biopharmaceuticals (e.g., mAbs), some specific methods need to be developed because of the structural complexity of ADCs and the presence of their cytotoxic agents. As a results, a significant number of methods for the physicochemical characterization of unique features of ADCs, including those used in the characterization of drug-load profile and distribution, the average DAR, the amount of unconjugated mAb and unconjugated payload-related species have been continuously developed and reported [MAbs. 2015 December 14:1]. It highlights the fact that no single technique can satisfactorily provide sufficient information about the ADC molecules. On the other hand, while physicochemical techniques can produce information about structure and composition and are used to monitor content, purity, and chemical stability of ADC, product physicochemical techniques cannot yet predict the biological activity of ADCs. Thus, a combination of physicochemical, immunological, and biological methods seems necessary in order to account for its identity, purity, concentration, and activity (potency or strength) for any ADC samples.

There has been increasing interests in the biopharmaceutical industry to develop biosimilars (including mAbs and ADCs) in order to bring less expensive biotherapeutics to market throughout the world.[5] The clinical and commercial success of Kadcyla and Adcetris, on the one hand, validates the ADC as a therapeutic approach; it also prompts vast interests in developing their biosimilars. On account of the increasing level of ADC sample complexity that comes from the heterogeneity of the conjugation, critical quality attributes (CQAs) that are linked to the conjugation process seems to be unique to this type of molecules, and deserves to be taken into account and should be paid a close attention when assessing the ADC biosimilars. These include the drug distribution, the average number of drugs on the antibody (drug to antibody ratio), drug related impurities, potency, un-conjugated mAb, conjugation site and site occupancy, to name a few. These CQAs of an ADC product is directly linked to the target site specificity, binding properties, the in vitro and in vivo stability of the linker and drug, which in turn determines clinical efficacy and safety of an ADC.[6] Because of its intrinsic complexity, those CQA can only be acquired through extensive characterization of ADCs via a combination of physicochemical, immunological, and biological methods. The establishment of the CQA is vital for developing the biosimilar ADCs to ensure its comparability with the innovator and product safety.

Figure 3:
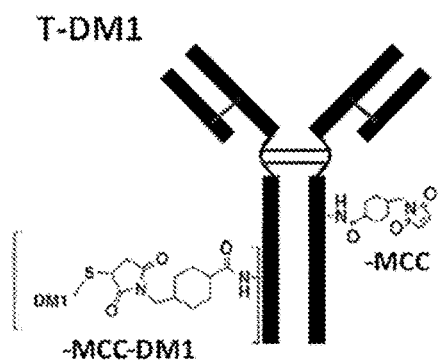
FIG. 3 is a schematic of T-DM1 conjugation wherein the lysines on trastuzumab are modified with SMCC linker and subsequently reacted with the sulfhydryl of the DM1 drug. MCC-DM1 represents MCC-DM1 and MCC represents the linker. MCC-DM1=956.3644, MCC=219.0895
Figure 4:
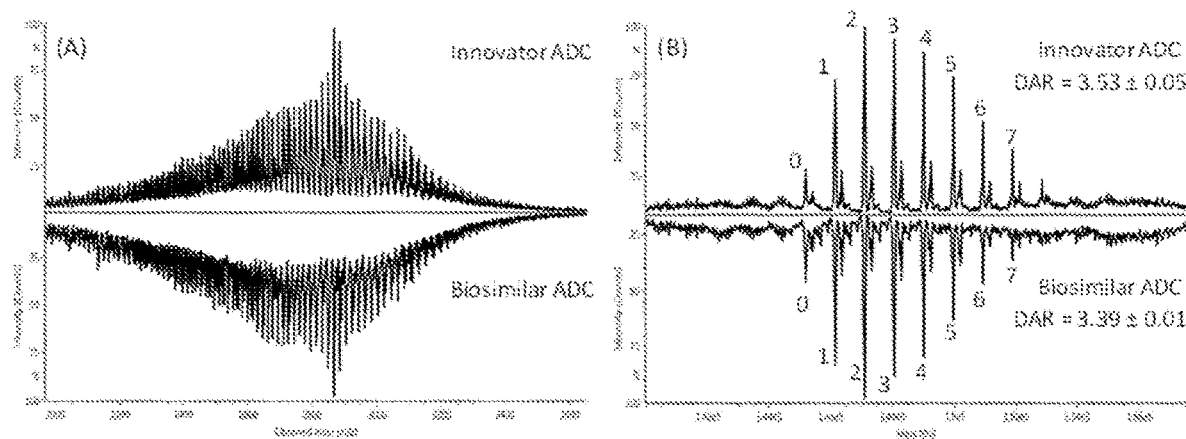
FIG. 4 is an intact mass comparison between the deglycosylated innovator ADC and the deglycosylated biosimilar candidate ADC: (A) the combined raw mass spectra mass spectra with m/z range of 2200-3600; and (B) deconvoluted mass spectra (processed by UNIFI 1.8 using MaxEntl) Both ADC have been treated with PNGFase. The label 0, 1, ..., n correspond to the Tmab linked with n number of DM1 molecules through a linker. DARs are calculated and shown on the plot.

The US Food and Drug Administration (FDA) approved T-DM1 for the treatment of HER2+ breast cancer [http://www.fda.gov/Drugs/InformationOnDrugs/ApprovedDrugs/ucm340913.htm]under the brand name Kadcyla in 2013. T-DM1 consists of the therapeutic anti-HER2 monoclonal antibody trastuzumab (Tmab) covalently linked to the maytansine derivative (DM1) via a linker as shown in FIG. 3. The lysine conjugates ADC, like T-DM1 utilizes the solvent-exposed ε-amino groups of lysine residues to attach the drugs. Tmab contains 88 lysines and 4 amino terminal groups that could be modified through the conjugation steps. Due to the heterogeneous nature of lysine conjugation chemistry, the resulting conjugates consists of subpopulations that differs in the number of drugs attached as well as the location of the drug linkage. Previous studies with T-DM1 or other antibody-DM1 conjugates have given some insight into the drug distribution, load and location of conjugation sites of the conjugates. A report on this particular ADC drug suggests that an average of ~3.5 DM1 molecules are conjugated with every one Tmab antibody and at least 70 lysine sites on Tmab are partially conjugated with the drug. However, the list of conjugation sites and relative site occupancy has not been described, and the effect of the lysine conjugation sites and relative site occupancy on the various attributes of T-DM1 is unknown.

Presented herein are the results on the extensive characterization of T-DM1 by a combination of analytical methods. Shown herein is a set of analytical methods that are specific and sensitive to determine the structures of T-DM1 that are manufactured by two different companies; to compare the analytical results to assess the structural similarity of the T-DM1 samples, and to evaluate the bioactivity and the cytotoxicity of the T-DM1, thus contributing to the analytical strategies for monitoring the development of ADCs and their biosimilars LC/MS results for the ADC samples on their primary amino acid sequence, drug to antibody ratio (DAR), conjugation sites and site occupancy are reported and compared. Furthermore, thermal stability, free drug content, and impurities were analyzed to further to determine the comparability of the two ADCs. Lastly, the biological activities were compared between the innovator and biosimilar ADCs using cytotoxic activity assay and HER2 binding assay.

Experiment 1 is an embodiment of the invention disclosed herein. Experiment 1 is design to analyze the site occupancy ratios of certain ADC samples using the workflows as disclosed in FIGS. 1 and 2.

Experiment 1

Sample and Materials

The innovator and candidate biosimilar antibody drug conjugates T-DM1 were provided by a Chinese pharmaceutical manufacture. Iodoacetamide (IAM), dithiothereitol (DTT), urea, tris-hydrochloride (tris-HCl) were purchased from Sigma-Aldrich (St. Louis, Mo., USA). Sequencing grade modified trypsin and Asp-N were purchased from Promega Corporation (Madison, Wis., USA). Formic acid, acetonitrile (ACN, Optima LC/MS grade) and H$_2$O (Optima LC/MS grade), and tris hydrochloride solution (1 M, pH 7.5) were obtained from Fisher Scientific (Pittsburgh, Pa., USA). illustra NAP-5 columns were purchased from GE Healthcare (Pittsburgh, Pa., USA).

Peptide Mapping Analysis

Tmab (1 mg/ml) and T-DM1 (1 mg/ml) were denatured in 6.5 M guanidine chloride, 0.25 M Tris, pH 7.5. The denatured antibody solution was mixed with 500 mM DTT to a final concentration of 3 mM and incubated at room temperature for 45 minutes and then alkylated by adding 500 mM iodoacetamide stock solution to a final concentration of 7 mM incubated at room temperature in the dark for 40 minutes. Buffer exchange (0.1 M Tris, 1 M urea, pH 7.5) was performed using a NAP-5 column (GE Healthcare). Sequencing grade modified trypsin or Asp-N was added to each sample (enzyme to protein ratio 1:25, w/w) and incubated at 37° C. for 5 hours. The digested peptide mixture was diluted to 0.45 µM. Leucine enkephalin (LeuEnk, sequence YGGFL) was added to the mixture at the final concentration of 0.05 µM. The injection volume for each LC/MS run was 5.0 µl.

LC/MS Instruments and Bioinformatics

Intact protein and enzyme digests of Tmab and T-DM1 were analyzed in triplicate using an ACQUITY UPLC H-Class Bio System coupled with a Xevo G2-XS QToF mass spectrometer equipped with a lockspray ion source (Waters Technologies Corporation, Milford, Mass.). Intact protein samples were separated with a ACQUITY UPLC Protein column (2.1 mm×50 mm BEH300 C4 1.7 µm Waters Technologies Corporation, Milford, Mass.) using a 10 min linear gradient at a flow rate of 0.200 mL/min. Peptides from protein digests were separated with a ACQUITY UPLC peptide column (2.1×100 mm BEH300 C18 1.7 µm, Waters Technologies Corporation, Milford, Mass.) using a 60-min linear gradient at a flow rate of 0.200 mL/min. Mobile phase A was water with 0.1% formic acid, while mobile phase B was acetonitrile with 0.1% formic acid. For the data acquisition during the peptide analysis, the Xevo G2 XS QToF mass spectrometer was operated either in the MSE or FastDDA modes. For the MSE mode, the instrument was alternating between the low energy and high energy scans (0.5 sec per scan), which was used to generate intact peptide ions and peptide product ions, respectively. A collision energy ramp between 20 V and 45 V was used for fragmenting peptides in high energy scans. Glu-fibrinopeptide standard (Waters Technologies Corporation, Milford, Mass.) at a concentration of 100 fmol/µL (m/z 785.8426) was continuously infused at a flow rate of 10 µL/min through the lockspray channel, and the lockmass signal (for 0.5 sec) was acquired at every 30 s to provide the external mass calibrant.

The LC/MS raw data for peptide analysis was processed using UNIFI Scientific Informatics System (Version 1.8) to generate precursor masses as well as the associated product ion masses (charge state reduced and de-isotoped) for subsequent protein identification and quantification. The following criteria are used in the identification of conjugated peptides during the current analysis (i) Mass accuracy for the matched precursors is within 5 ppm of mass error; (ii) There are at least 3 primary fragment ions matched for each identified peptide, (iii) Signature fragments (m/z, 547.2) corresponding to the drug payload are observed for conjugated peptides.

For peptide quantification, extracted ion chromatographic (XIC) peak areas that correspond to all the charge states, and all the specified adduct ions of each peptide were combined as a single measure to quantify the abundance of the peptide and its conjugated isoforms). All the peak areas was normalized against the peak areas of the spiked-in internal standards, and triplet injections were performed for each sample. The relative site occupancy was calculated using the equation:

$$\text{Site occupancy} = \text{peak area (conjugated pep. peak)}/[\text{Area(unconjugated pep. Peak)} + \text{Area (Unconjugated pep. peak)}] \quad (1)$$

Results

Identification of Conjugation Sites by Peptide Mapping Approach

Figure 5:
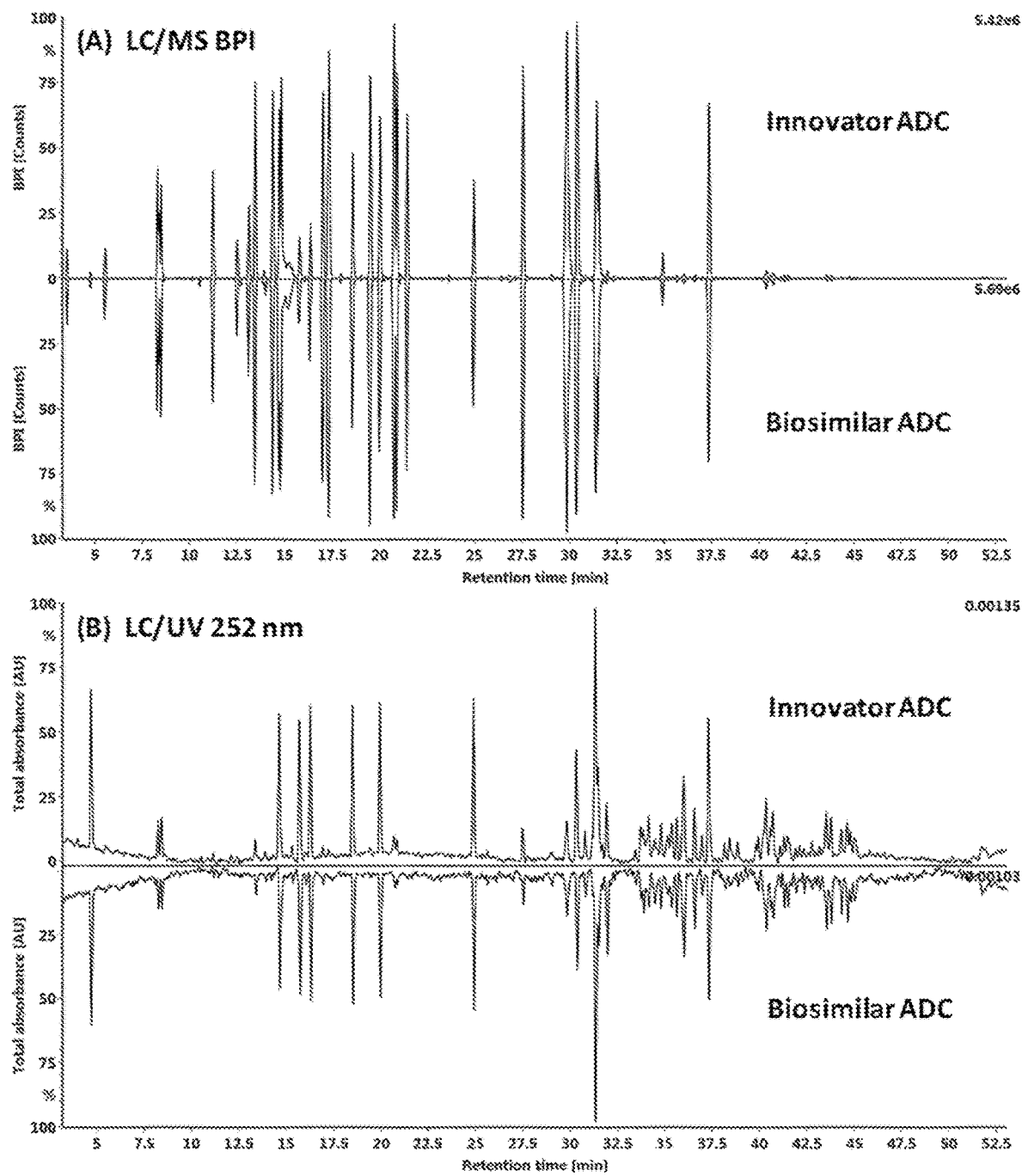
FIG. 5 represents mirror plots of LC-MS$^E$ tryptic peptide maps of the innovator and biosimilar for tryptic digests. (A) LC/MS base peak intensity chromatogram (BPI). (B) LC/UV 252 nm.

Lysine-conjugated ADC and unconjugated mAb were treated separated by either trypsin or Asp-N. The digests were separated by RP-chromatography and followed by UV and MS analysis in tandem for peptide identification. For each digest, fragmentation data were collected either in data independent acquisition in $MS^E$ mode or data dependent acquisition (DDA) modes to acquire sequence information about the observed peptides. For low abundant conjugated peptides, $MS^E$ and DDA spectra jointly serve the purpose to identify the conjugate peptides as well as locate the conjugation sites. FIG. 5 shows the comparative (mirror) plots of LC-$MS^E$ tryptic peptide maps from the innovator and biosimilar ADC digests in either (A) MS base peak chromatogram or (B) UV absorbance chromatogram at 252 nm. All the conjugated peptides elute later in the gradient and appear from 30 min to 52 min in the chromatogram, due to their increased hydrophobicity caused by the payload moiety. Upon conjugation, modified lysine residues are no longer trypsin cleavable. As a result, the majority of the tryptic peptides with conjugated payloads are peptides containing one missed trypsin cleavage sites, with exception of lysine followed by a proline; whereas the peptides from Asp-N digestion typically do not contain miss cleavages. Therefore, a majority of the conjugated peptides from trypsin digestion only encompass a single conjugated lysine (unless it was next to a C-terminal proline), whereas Asp-N digestion can generate peptides with multiple lysine residues (up to 9) creating a mixture of Asp-N peptides with the same sequence but different conjugation sites (positional isomers). These positional isomers can complicate the specific site determination of the conjugated Lys residues, and require more complete sequence coverage in the high energy fragmentation spectrum. Consequently, a combined fragmentation data from the two enzymatic digests is needed to furnish the full sequence coverage of light and heavy chains for both ADC samples. For all identified conjugation sites only partial modification with drug payloads are observed, i.e., both modified and unmodified peptides were discovered in the experiment. Overall, lysine conjugation sites identified by the two enzymatic digestions were consistent.

Notably, the conjugation sites found in the biosimilar ADC are consistent with sites in innovator ADC. Table 1 shows the summary table for the conjugation sites identified in T-DM1 in innovator and biosimiar ADCs. For T-DM1, there are 92 possible Lysine conjugation sites available (88 lysine residues and 4 N-terminal amine groups), out of which 82 sites were confirmed to be partially conjugated. Furthermore, 3 sites were identified containing just conjugated linkers, as shown in Table 2, which are located at heavy chain K136, K213, and K225, each of which corresponds to the sites with one MCC linker that was not modified with DM1.

Figure 6:
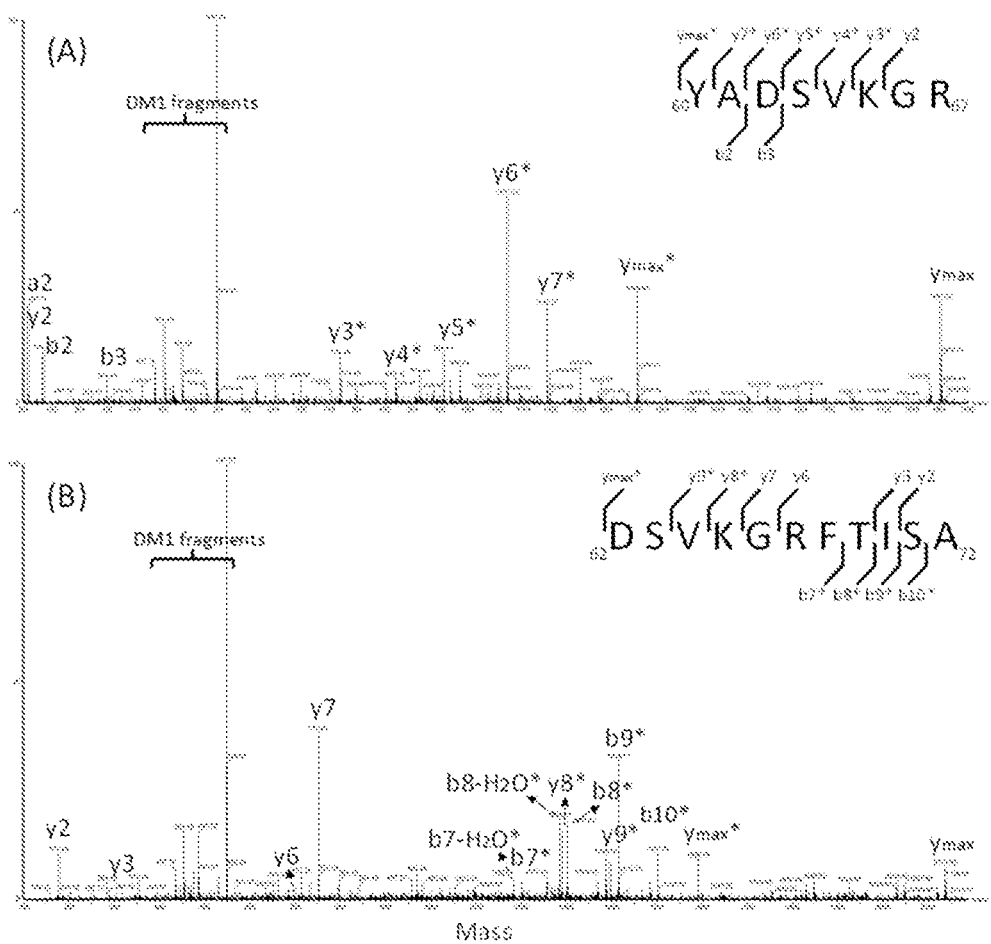
FIG. 6 is a deconvoluted MS/MS spectrum of peptides containing lysine site K65. (A) tryptic peptide HC60-67. (B) Asp-N peptide HC62-72.
Figure 7:
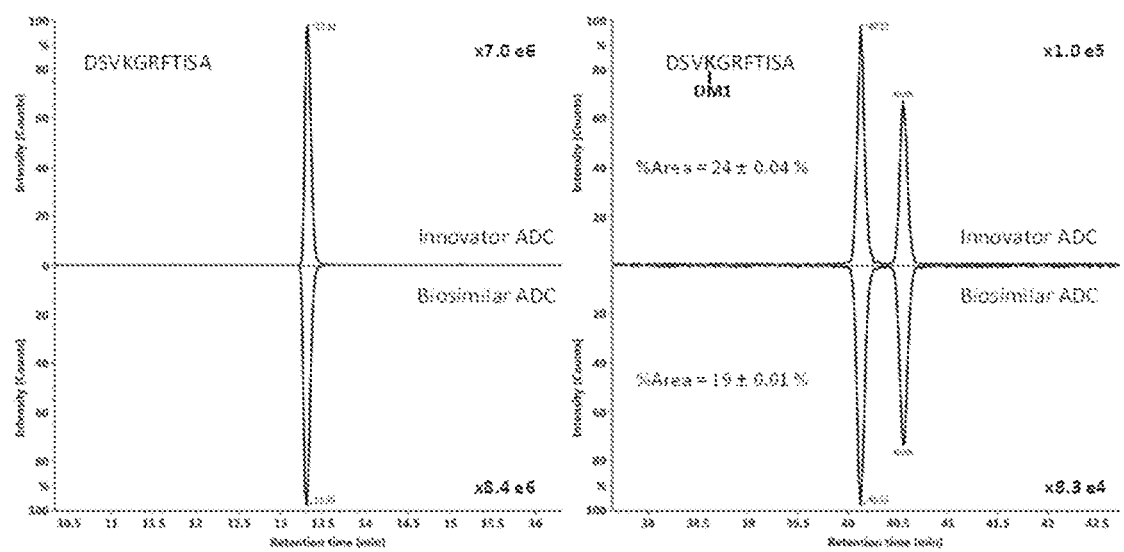
FIG. 7 shows mirror plots of extracted ion chromatograms (XIC) of (A) unconjugated CDR peptide and (B) conjugated peptide with DM1 containing site K65 from Asp-N digest for the innovator and the biosimilar ADCs. The relative peak area of the conjugated peptides is calculated and labelled on the plot.

The CDR region of Trastuzumab contains one lysine residue, which is located at the heavy chain K65. Both trypsin and Asp-N peptide mapping analysis confirm the heavy chain K65 site is partially occupied by DM1 payload. MS/MS spectra from tryptic peptide and Asp-N peptide containing the conjugated K65 site are shown in FIG. 6. The CID fragmentation spectra of the conjugated peptides show a series of signature fragments at m/z of 547.2, 485.2, 453.2, and 437.2. These signature fragment peaks all show typical isotope patterns produced by compounds containing halogen elements, suggesting these peaks derive from the chlorine-containing DM1 drug. Tmab-DM1 conjugated peptides also show another characteristic chromatographic behavior that is important to consider for identifying conjugated peptides. Peptides with the conjugated DM1 drug are eluting in pairs, which attributes to the different stereochemical configurations caused by the antibody drug linkage through a maleimide. FIG. 7 shows the extracted ion chromatogram comparison of the CDR region peptide ($^{62}$DSVKGRFTISA$^{72}$) from Asp-N digestion between the innovator and biosimilar at its conjugated or native form. The diastereomers of the conjugated peptide show two peaks at 40.13 and 40.55 min respectively as shown in FIG. 7 (B). The percent areas of the conjugated peptides over the sum of the unconjugated peptides and conjugated peptides were 24±0.04% and 19±0.01% for the innovator and the biosimilar ADCs respectively.

Quantification of the Conjugated Peptides

Figure 8:
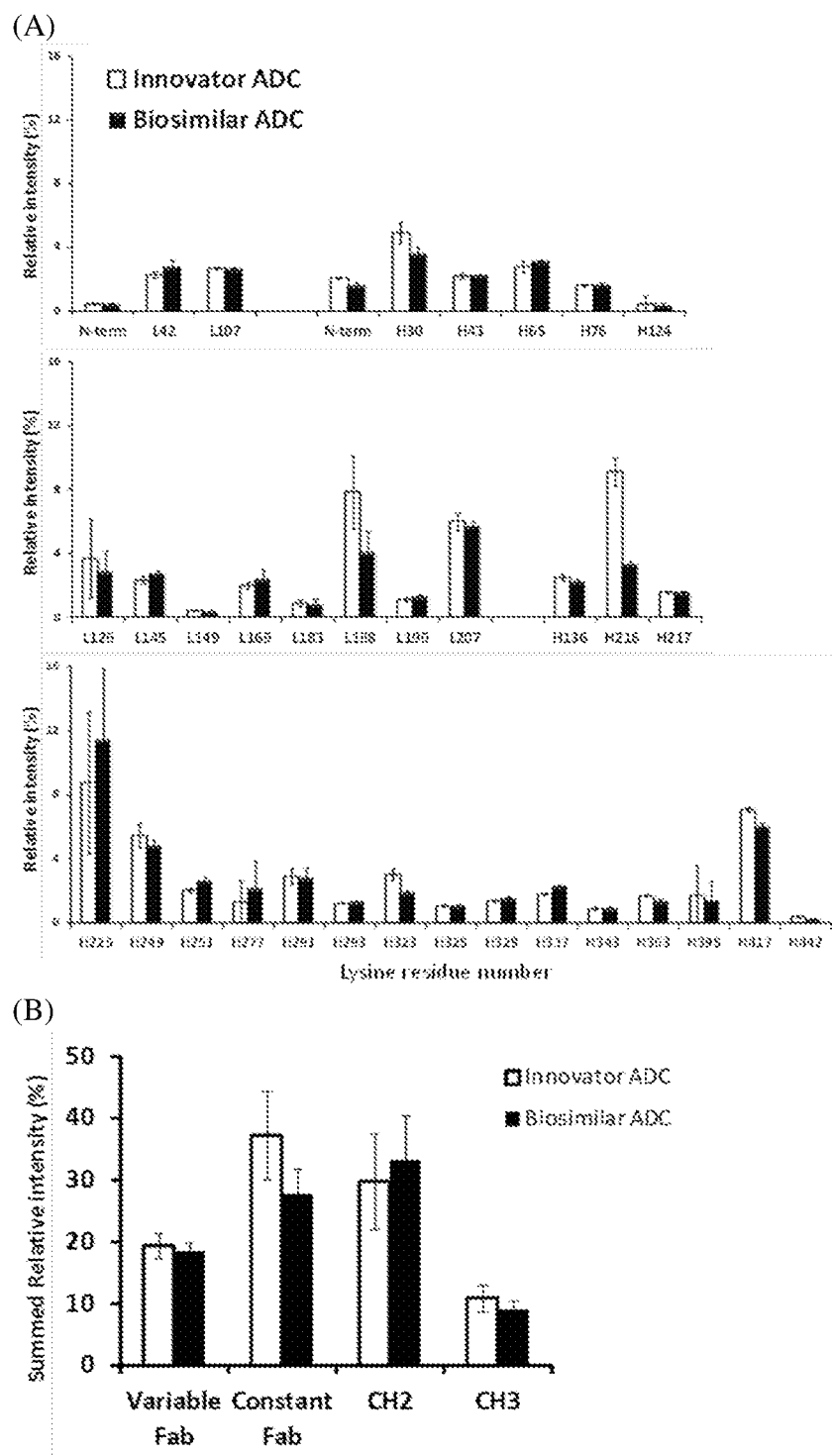
FIG. 8A shows the relative peak areas of the conjugated peptides from tryptic digest comparing the innovator and biosimilar ADCs. The site of lysine conjugation is labeled on the X axis.
FIG. 8B shows the sum of intensity of the conjugated peptides in each region, i.e. Variable Fab, Constant Fab, $CH_2$ and $CH_3$.

To access the conjugation level of the innovator and biosimilar ADCs at the individual site, the intensity of each conjugated tryptic peptides were used compared. A known amount of peptide (leucine enkephalin, sequence YGGFL) was spiked in to each sample as the internal standard to normalize the intensity of conjugated peptides. Relative intensities of identified tryptic conjugated peptide are shown in FIG. 8. The quantification results were grouped and presented according to different domains of antibodies. FIGS. 6A and 6B present variable domains ($V_H$, $V_L$), constant regions ($C_H1$, CO and Fc ($C_H2$ and $C_H3$) regions respectively. Since the majority of the tryptic conjugated peptides are with only one payload, the tryptic conjugated peptides to quantify the individual site conjugation level can be used. The sites with less conjugation level for the biosimilar than the innovator are H30 (residue 30 on the heavy chain) in the $V_H$, L188 ($C_L$), H216 ($C_H1$), H323, H363, H417 ($C_H2+C_H3$). On the other hand, L145 ($C_L$) and L169 ($C_L$) and H337 ($C_H2$) show slightly higher conjugation level in biosimilar candidate ADC.

Discussion

LC-MS based approaches have been successfully applied to define the molecular similarity between innovator mAb and a biosimilar.[5,10] Due to the additional heterogeneity caused by the conjugation, ADCs exhibit an increased level of complexity comparing with the antibody. To demonstrate molecular and product equivalency of an ADC biosimilar with an innovator, advanced and more sensitive analytical technologies over the current state of the art are needed. In the technologies and methods discussed herein, detailed structural characterization including intact mass analysis, DAR measurement, conjugation site identification, and site occupancy to determine the molecular similarity of innovator and biosimilar ADC is now possible. To examine other product attributes between the candidate biosimilar and the innovator ADCs, a series of physicochemical and biological methods was applied to compare high order structure, product impurity, free drug content, and biological activity.

First, intact mass analysis serves a fast way to examine and compare the mass, general drug load/distribution pattern as well average DAR values between the innovator and biosimilar ADC. DAR is one of the most important product quality attributes of an ADC. It determines the amount of drug that can be delivered to the target cell, which directly affect safety and efficacy. Depending on the conjugation chemistry and the types of ADCs, different strategies have been implemented for DAR measurement, including UV/VIS, MALDI-TOF-MS, LC/UV, capillary IEF, UV-MALDI, HIC, IMMS [mAbs. 2011; 3(2):161-172, Protein Science. 2015; 24(8):1210-1223, J Am Soc Mass Spectrom. 2015 October; 26(10):1791-4]. One advantage of MS-based analysis for the analysis of ADCs is its independence of the spectroscopic nature of the linker and payload [J Am Soc Mass Spectrom. 2015 October; 26(10):1791-4]. Lysine-conjugated ADCs is much most challenging for DAR determination due to its high level of heterogeneity. To date, there are limited numbers of studies reported on DAR characterization on lysine-conjugated ADCs [Protein Science 2005; 14(9):2436-2446, Bioconjugate Chemistry. 2014; 25(7): 1223-1232]. Intact mass spectra clearly demonstrated T-DM1 is a mixture of species with different DARs ranging from 0 to 7. The difference in DAR observed in the intact mass analysis suggests the average number of payload per antibody is slightly different between the biosimilar and the innovator T-DM1. The cause of this variation could be owing to the difference of conjugation sites or/and site occupancy. DAR values are calculated from the relative MS intensity of the conjugated antibodies and unconjugated antibodies. Without considering the difference in ionization efficiency between the naked antibody and the conjugated antibody, the MS-derived DAR can be different from the true DAR. Hence, DAR determined by RP-LC/MS can be used for lot-to-lot comparison for lysine conjugates. However, the DAR value needs to be verified by an orthogonal technique.

Peptide mapping is routinely used for confirming the amino acid sequence and characterizing the post translational modifications for antibodies and other recombinant proteins.[11] It has also been applied to determine the chemical conjugation sites of ADCs.[12] There are very few studies in the literature reporting the conjugation site of lysine-conjugated ADC. Conjugation sites of huN901-DM1, another humanized IgG1 antibody with maytansinoid conjugated to lysine residues by the similar linker chemistry, were reported by Wang et al. Out of 86 lysine residues, 40 different sites on the IgG1 antibody were identified with covalently-linked DM1. Eighty-two 82 conjugated DM1 sites on Tmab were identified, including the 4 N-terminus amine groups among a total of 92 Lys sites that could possibly be modified by the DM1 drug. In addition, three sites with linker-only are identified and all are located on the heavy chain. The existence of ADC species that contain some MCC linker-only sites was also demonstrated by intact mass analysis (FIG. 2), in which peaks with additional 219 Da were observed next to each of the primary peak. The incomplete conjugation in the second conjugation step of a two-step conjugation process, where linker—modified intermediate reacted with DM1, may contribute to the linker-only sites present on the antibody.[4] In addition, early studies suggested that tyrosine and histidine residues can also be modified by succinimide ester.[13] All the lysine residues in $C_H2$ domain are modified with the drug at various levels.

This observation is consistent with the previous studies showing that the lysine residues in $C_H2$ domain for IgG1 exhibit a high degree of solvent accessibility and flexibility.[12] There are two lysine residues in the hinge region, $K^{221}$ and $K^{225}$. No $K^{221}$ is observed being modified by the linker or the linked-payload, which could be attributed to the steric hinderence caused by the modified $K^{225}$ in their proximity. There were no evidence of conjugation for 5 lysine residues on half body (containing one light chain and one heavy chain). Out of those 5 sites, there are 1 in the $V_L$ (Light chain $K^{39}$), 2 in the $C_H3$ region (Heavy chain $K^{373}$ and $K^{412}$), 1 in $C_H1$ (Heavy chain $K^{150}$), and 1 in the hinge region (Heavy chain $K^{221}$). The failure to detect the conjugated peptides from the 5 sites most likely suggests that the conjugation level at these sites is significantly lower than the other identified sites.

Conclusion

In summary, a detail structural characterization of T-DM1 was presented, including establishing the drug load profile, localizing and profiling the individual drug conjugation site. These structural characteristics were compared between a biosimilar candidate ADC and the innovator to define the molecular similarity. The discrepancy observed can affect the binding properties of the antibody. Being critical to the clinical efficacy of the ADC, these attributes needs to be closely assessed for development of a biosimilar. Furthermore, other product attributes were also compared, including high order structure, monomer content, free drug content, and biological activities. In the development process of a biosimilar, it is important to understand these critical quality attributes and choosing the appropriate analytical and bioanalytical techniques to better characterize and assess the similarity of the product to ensure the product quality during manufacturing.

Experiment 2 details further analyses of the ADC samples discussed herein using various analytical techniques. The analyses detailed in Experiment 2 are also considered embodiments of the invention disclosed herein.

Experiment 2

Intact Mass

Un-conjugated Trastuzumab (Tmab) and T-DM1 solution were diluted to a concentration of 1 mg/mL in 100 μl 1 M tris-HCl buffer (pH=7.5). 2 μl of PNGase F (Waters Technologies Corporation, Milford, Mass.) solution was added into each sample and the reaction mixture was incubated for 20 hours at 37° C. The incubated solution was diluted with 3% acetonitrile, 97% H2O, 0.1% formic acid to final concentration of 0.5 mg/mL. Total 0.5 μg of Tmab or T-DM1 was injected for each LC/MS run.

Differential Scanning Calorimetry (DSC)

Thermal analysis of the ADC samples was performed using MicroCal VP-Capillary DSC. Each ADC sample was diluted to 1.0 mg/ml by addition of PBS. The instrument scanned each sample over the temperature range 25 to 110° C. at a rate of ?? ° C./min. Data analysis was done using Origin 7.

Free Drug Analysis

The ADC samples (50 μl each) were treated with cold 100 μl methanol and incubated for 30 min in ice bath. The samples were then centrifuged at 13,000 rpm for 30 min and the supernatant was subject to further analysis using reversed phase liquid chromatography. The standard curve was generated using serial dilution of DM1 standards stock solution. The free DM1 amount is calculated by the following equation:

$$\text{Free DM1\%} = \text{moles of Free DM1}/(\text{DAR} \times \text{moles ADCs}) \quad (2)$$

Size-Exclusion Chromatography (SEC) SEC experiments were performed on Waters2690 system using TSK G3000SWXL (300×7.8 mm, Sum). The mobile phase was 0.2 M tripotassium phosphate, 15% isopropyl alcohol at 0.5 ml/min flow rate. The UV absorbance was measured at a wavelength of 280 nm.

Capillary Sodium Dodecyl Sulfate Gel Electrophoresis (CE-SDS)

Beckman PA800 plus system was used for CE-SDS with with Beckman capillary (50 um ID×65 cm) to analyze the ADCs samples. All samples were diluted to 1.0 mg/ml with water. 50 ul of each ADC sample was mixed with 100 ul of SDS sample buffer and 5 ul of 500 mM iodoacetamide. The mixture was heated at 70° C. for 10 min before injection. The instrument was operated at a voltage of 15 kV for protein separation and the UV detection was recorded at 220 nm.

Cell Proliferation Inhibition Assay

BT-474 cells at the logarithmic growth phase were treated with 0.25% Trypsin-EDTA. Cells were resuspended in 10% FBS-DMEM/F12 medium with cell density at $1.5 \times 10^5$/ml, and seeded in 96-well cell culture plate (100 μl per well). Serial dilution of 1:2 folds was done using 10% FBS-DMEM/F12 culture medium to a final concentration of 0.039 μg/ml. The series of dilute samples were transferred into BT-474 cell culture plates that have been inoculated (50 μl per well). The plates were incubated at 37° C. in a humidified 5% $CO_2$ incubator for 5 days. After incubation, each well was treated with 10 μl CCK-8 solution followed by incubation for 4 hours. The absorbance at 450 nm was recorded using SpectraMax M5 microplate reader.

Surface Plasmon Resonance

The binding to HER2 protein was evaluated by SPR using Biacore T200. FcRn was immobilized to a CMS sensor chip surface via the amine coupling method. Each ADC sample was diluted to 5 μg/ml with 1×HBS-EP buffer, with a flow rate of 5 μl/min to flow through flow cell 2. The HER2 protein was serially diluted with 1×HBS-EP buffer and injected into the ligand-immobilized CMS chip with the injection time of 120 seconds and dissociation time 1500 seconds. The data was globally fitted using 1:1 binding model. The $K_D$ value was evaluated using Biacore T200 software (v2.0).

Results

Intact MS Analysis

Antibody drug conjugates are a complex mixture of conjugated species, which differ in the number of payloads attached as well as the attachment sites of the payload on the mAb. The distribution of the payload was determined by intact mAb LC/MS analysis. To reduce the complexity of ADC molecules, the ADCs samples were treated with PNGase F to remove the N-glycans. After the de-glycosylation step, samples from either innovator ADC or a candidate biosimilar ADC were analyzed by reversed phase (RP) LC/MS. FIG. 2 shows the raw mass spectra mass spectra with a m/z range between 2200 and 3600 Da and the MaxEnt 1 deconvoluted mass spectra for the innovator ADC and the candidate biosimilar ADC, respectively. The deconvoluted mass spectrum of the innovator ADC displays 8 major peaks with a mass difference of 957 Da observed between adjacent peaks. This mass difference matches the combined mass of a covalently linked DM1 drug with one MCC linker (DM1+MCC, MW 956.36 Da). The masses of 8 major peaks in both deconvoluted spectra (the innovator and candidate biosimilar ADCs) correspond to the masses of Tmab with 0 to 7 DM1 payloads and linkers respectively (labeled as +0, +1, etc). For every major peak in the deconvoluted peak, a lower intensity peak with 219 Da shift is also observed. These smaller peaks are attributed to the linkers that are conjugated to the mAb molecules but are yet reacted with DM1 payloads. The ion intensity of between the corresponding MS peaks (by mass) in the spectra differs slightly between the two samples, which could be due to the slight mass load differences onto the RP column. Average DARs can be determined by the weighted peak areas of all the peaks in the MS profiles The MS derived DAR value from the innovator ADC is 3.53±0.05, which agrees very well with reported values of Kadcyla.[4] The candidate biosimilar ADC shows a slightly smaller DAR value of 3.39±0.01.

Higher Order Structures (DSC)

Figure 9:
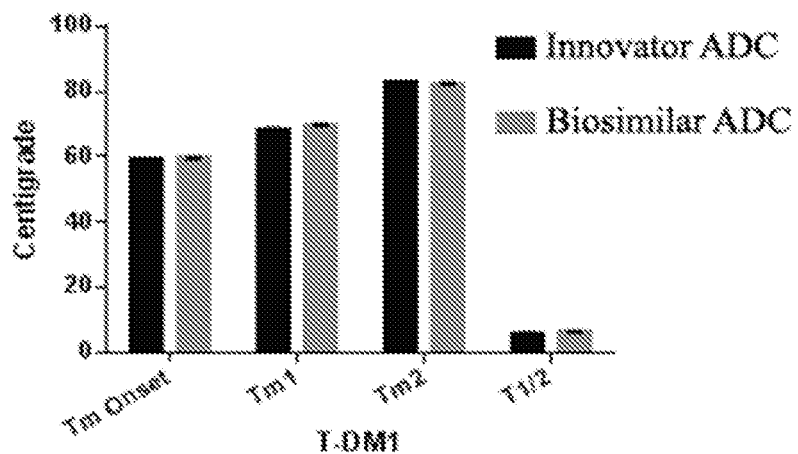
FIG. 9 depicts the DSC thermograms of the ADC samples

The thermal stability of innovator ADC and biosimilar ADC were evaluated by DSC. All the ADC samples were analyzed in the same buffer solution with the concentration at 1 mg/ml. The DSC thermograms for all the ADC samples are displayed in FIG. 9. There are two major transitions observed for all the samples. The first transition temperature for biosimilar ADC is about 1.5° C. higher than this innovator ADC. The first transition (Tm1) for biosimilar ADCs occurred at 69.84±0.03° C., whereas the same transition for innovator ADC occurred at 68.55±0.13 and 68.34±0.04 for two batches. The second transition (Tm2) is very close for both (within 0.5° C.).[7,8]

Size Variants

Figure 10:
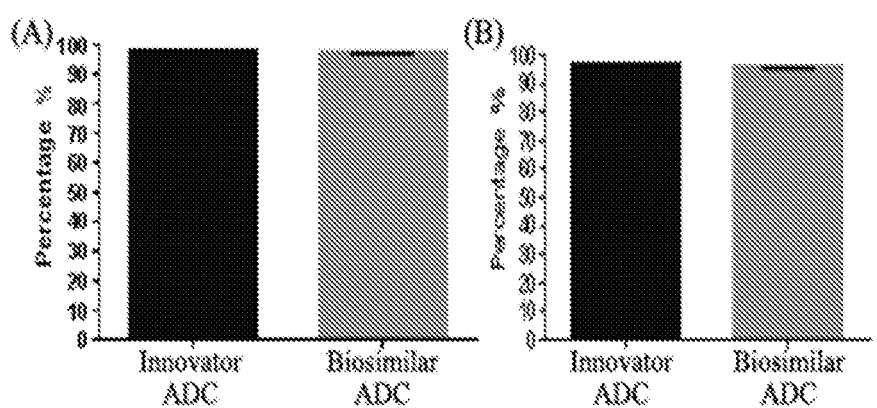
FIG. 10A shows the SEC-HPLC analysis of aggregate content of the ADC samples.
FIG. 10B shows the CE-SDS analysis of the ADC samples under reduced conditions.

The aggregate content of the ADC samples was determined by two orthogonal methods, SEC-HPLC and CE-SDS. The results from SEC-HPLC (FIG. 10) exhibit predominant monomer content (>95%) for both innovator and biosimilar candidate. SEC-HPLC results show two batches of innovator have higher monomer content (98.30±0.03% and 98.20±0.02%) than biosimilar candidate ADC (96.9±0.03% and 96.61±0.02%). Similar to the SEC-HPLC results, CE-SDS analysis under reduced conditions showed predominant monomer contents for all ADC samples (as shown in FIG. 11). Two batches of the innovator ADC exhibit 96.63±0.07% and 96.23±0.13% monomer purity, respectively, while two batches of the biosimilar ADC show 95.43±0.08% and 93.48±0.14%.[9]

Un-Conjugated (Free) Drug Analysis

Figure 12:
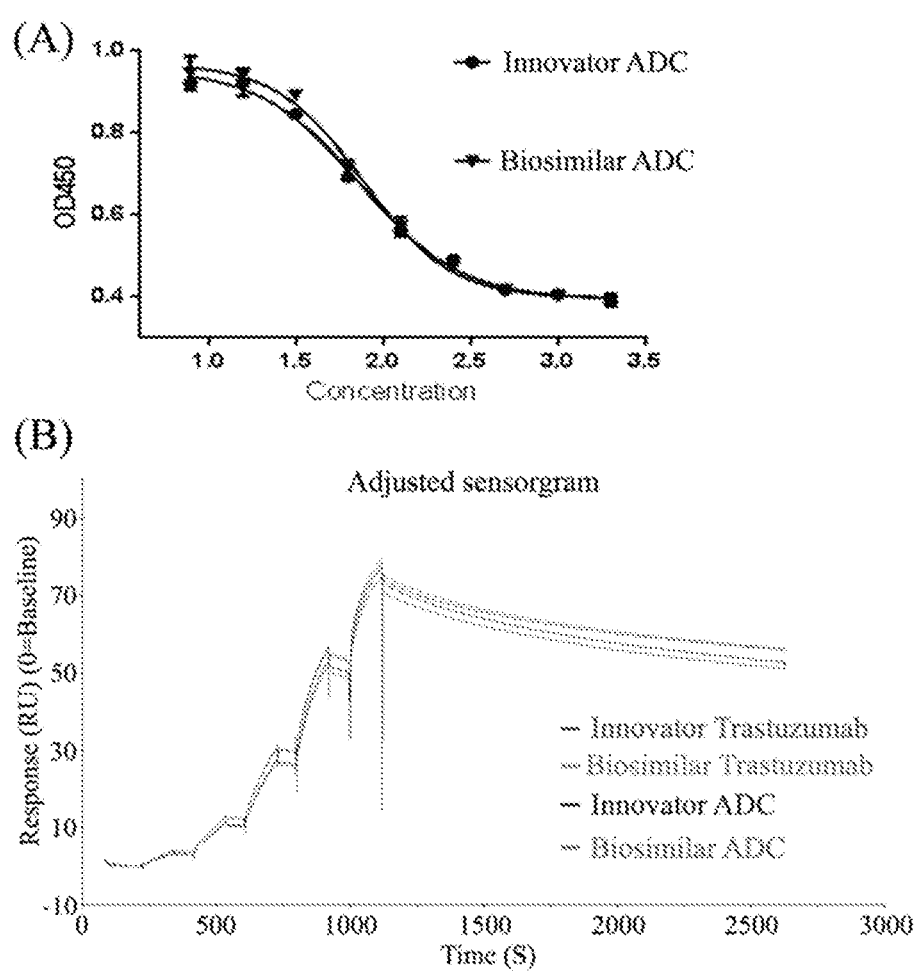
FIG. 12A is a plot of the cytotoxic activity of the ADC samples.
FIG. 12B is a plot of the binding activity of the ADC samples to HER2 protein.

Because the small molecule drug payload in an ADC sample is generally highly potent and very toxic, the quantity of unconjugated (free) drug is an important product quality attributes that is directly related to product toxicity and patient safety. The final product may contain residual free drug or drug-related impurities as result of incomplete removal. It is therefore essential to characterize and quantify free drug content. Quantification of free drug in the ADC samples was performed by reversed-phase chromatography after protein precipitation. The free drug contents of the ADC samples are shown in FIG. 12. The two batches of the innovator ADC shows the abundance of free drug accounts for 1.15±0.05 and 0.82±0.05% in molar ratio, while biosimilar ADC 1.88±0.05% and 1.33±0.06% (molar ratio) for the two selected batches.

Biological Activities

Compared with mAbs, an ADC is more complex in structure, in addition to the structural comparison of ADCs between innovators and biosimilar, the biological activity of the ADC was evaluated and compared using in vitro cytotoxic activity assay and HER2 binding affinity assay (SPR).

The cell proliferation inhibition assay was done using human breast cancel BT-474 cell. The results showed that the T-DM1 innovator and biosimilar exhibit the similar dose-effect relationship. The cytotoxic activity was measured to be 100.54% for one batch of innovator, 94.04% and 98.30% for two batches of biosimilar ADC against the reference innovator batch as shown in FIG. 13.

The binding to HER2 protein was evaluated by SPR using Biacore T200. $K_D$ reference (innovator) and samples (biosimilar) were (0.8123±0.0482) nM and (0.7684±0.0243) nM as shown in FIG. 14. The results suggest that the binding activity of the biosimilar is slightly less than the innovator.

Discussion

The CDR of Tmab contains one lysine residue (Heavy chain $K^{65}$), which is also found to be partially modified (Table 1). Without accounting for the ionization efficiency difference between the conjugated peptides and the unconjugated peptides, it is difficult to obtain the accurate site occupancy (the molar ratio) of the CDR lysine site. Modifications in the CDR region can potentially have a great impact on the binding properties of the antibody [MAbs. 2014 Mar. 1; 6(2): 327-339.] Hence the HER2 binding ability can be affected by the alteration of the CDR region caused by the conjugated payload drug. If the lysine site(s) in CDR is prone to be modified during the ADC preparation, the monitoring of the CDR peptides seems to be crucial to ensure the product quality.

It is worth noting that the same lys sites that bear both the conjugated linker-only and conjugated liner-payload moieties were identified for both innovator and biosimilar ADCs, indicating a certain level of consistency of the controlled conjugation process. However, the comparison of the relative abundance of the conjugated peptides/sites revealed the variation in the levels of conjugation between innovator and biosimilar ADC as shown in FIG. 8B. Specially, $C_L$ and $C_H1$ region showed the most significant difference (about 25%) between innovator and biosimilar, whereas $V_L$ and $V_H$ regions, $C_H2$ and $C_H3$ regions have no significant difference.

Although there is not a validated way to directly correlate the DAR value with the abundance of conjugated peptides at individual site, the overall abundance of all the identified conjugated peptide can be used to compare conjugation levels in two ADC samples along with the average DAR comparison. In the technologies and methods discussed herein, the DAR for biosimilar candidate ADC (3.39±0.01) is slightly less than innovator ADC (3.53±0.05), which is constant with the results from peptide analysis, where slightly lower abundance of conjugated peptides for biosimilar candidate is observed than innovator ADC.

DSC is a measure of thermal stability of proteins or antibodies by quantifying the thermal denaturation process. Thermal stability can be used to determine the melting temperature, stability, and purity of a given sample [J Biomol Tech. 2010 December; 21(4): 167-193.]. DSC is widely used for evaluation of pharmaceutical products [Curr Med Chem. 2005; 12(17):2011-20]. The specific application of DSC to the characterization of monoclonal antibodies has been discussed previously [J Pharm Sci. 2007 March; 96(3): 532-46.]. Such applications include formulation optimization studies,[14] the comparison of the innovator and biosimilars [mAbs 6:5, 1163-1177], and determining stabilizing effect of specific oligosaccharides PTM on mAbs[15] and pH dependence of conformational change[16]. A previous study published by Ionescu et al. showed that the first transition (Tm1) in Tmab represents the unfolding of the $C_H2$ domain, while the second transition represents melting the $C_H3$ and the Fab regions.[7] The decrease in Tm1 observed comparing Tmab and Tmab-DM1 was ~3.2 C, while the decrease in Tm2 was only ~0.1° C. (data not shown). The findings were consistent with another study, suggesting the conjugation of Tmab with DM1 has a greater impact on the thermal stability of the $C_H2$ domain the rest of the antibody.[8]

As demonstrated in previous studies, the level of aggregation of T-DM1 and Tmab was dramatically different.[8] The modification of the surface lysine residues with a large hydrophobic molecule like DM1 results in neutralization of the positive charge and significant increase in the hydrophobicity of the molecule. Since T-DM1 is prone to aggregation, monomer content has to be closely monitored due to process change or during manufacture. SEC-HPLC and CE-SDS demonstrated the monomer content is slightly lower in the biosimilar than the innovator. In addition, there is no significant difference in biological activity in terms of cytostatic activity and antigen binding activity observed between the innovator and the biosimilar ADC.

TABLE 1

Summary table of lysine conjugation sites identified in T-DM1. The innovator and the candidate biosimilar exhibit the same conjugation sites.

| Conjugated Lys Position | Tryptic Peptide | Sequence | RT (min) | | Therotical M + H⁺ (Da) | Mass error (ppm) |
|---|---|---|---|---|---|---|
| Light Chain | | | | | | |
| N-term NH₂ | 1: T1 | *DIQMTQSPSSLSASVGDR | 41.98 | 42.38 | 2835.2506 | 0.9 |
| 42 | 1: T3-4 | ASQDVNTAVAWYQQKPGKAPK | 33.77 | 34.21 | 3243.5474 | 2.7 |
| 45 | 1: T4-5 | APKLLIYSASFLYSGVPSR | 47.18 | 47.42 | 3025.5074 | 0.1 |
| 103 | 1: T7-8 | SGTDFTLTISSLQPEDFATYYCQQHYTTPPTFGQGTKVEIK | 41.49 | 41.77 | 5613.5723 | 0.4 |
| 107 | 1: T8-9 | VEIKR | 36.09 | 36.62 | 1600.7734 | -1.1 |
| 126 | 1: T10-11 | TVAAPSVFIFPPSDEQLKSGTASVVCLLNNFYPR | 51.80 | 52.00 | 4681.2688 | 1.4 |
| 145 | 1: T12-13 | EAKVQWK | 37.02 | 37.49 | 1844.8582 | -0.9 |
| 149 | 1: T13-14 | VQWKVDNALQSGNSQESVTEQDSK | 37.93 | 38.26 | 3633.6344 | -0.9 |
| 169 | 1: T14-15 | VDNALQSGNSQESVTEQDSKDSTYSLSSTLTLSK | 38.49 | 38.93 | 4576.0738 | 0.1 |
| 183 | 1: T15-16 | DSTYSLSSTLTLSKADYEK | 41.14 | 41.49 | 3065.3878 | 1.8 |
| 188 | 1: T16-17 | ADYEKHK | 31.38 | 31.99 | 1846.8011 | -3.0 |
| 190 | 1: T17-18 | HKVYACEVTHQGLSSPVTK | 30.84 | 31.23 | 3097.4452 | -3.9 |
| 207 | 1: T18-19 | VYACEVTHQGLSSPVTKSFNR | 35.70 | 36.02 | 3336.5358 | -2.3 |
| Heavy Chain | | | | | | |
| N-term NH₂ | 2: T1 | *EVQLVESGGGLVQPGGSLR | 44.67 | 45.03 | 2838.3673 | -0.1 |
| 30 | 2: T2-3 | LSCAASGFNIKDTYIHWVR | 41.35 | 41.55 | 3194.4769 | 2.7 |
| 43 | 2: T4-5 | QAPGKGLEWVAR | 39.99 | 40.38 | 2268.0812 | -2.0 |
| 65 | 2: T7-8 | YADSVKGR | 35.40 | 35.96 | 1851.8277 | -1.1 |
| 76 | 2: T9-10 | FTISADTSKNTAYLQMNSLR | 39.88 | 40.28 | 3217.4875 | 1.2 |
| 124 | 2: T12-13 | WGGDGFYAMDYWGQGTLVTVSSASTKGPSVFPLAPSSK | 46.32 | 46.65 | 4908.2543 | -0.4 |
| 136 | 2: T13-14 | GPSVFPLAPSSKSTSGGTAALGCLVK | 42.82 | 43.23 | 3445.6713 | -2.2 |
| 208 | 2: T15 | DYFPEPVTVSWNSGALTSGVHTFPAVLQSSGLYSLSSVVTVPSSSLGTQTYICNVNHKPSNTK | 43.58 | 43.82 | 7669.6789 | -3.1 |
| 213 | 2: T15-16 | DYFPEPVTVSWNSGALTSGVHTFPAVLQSSGLYSLSSVVTVPSSSLGTQTYICNVNHKPSNTKVDK | 41.96 | 42.20 | 8011.8692 | -4.4 |
| 216 | 2: T16-17 | VDKK | 34.43 | 35.09 | 1445.6676 | -0.6 |
| 217 | 2: T17-18 | KVEPK | 34.23 | 34.86 | 1556.7360 | -1.0 |
| 225 | 2: T19-20 | SCDKTHTCPPCPAPELLGGPSVFLFPPKPK | 40.40 | 40.78 | 4291.0066 | -1.3 |
| 249 | 2: T20 | THTCPPCPAPELLGGPSVFLFPPKPK | 44.86 | 45.11 | 3800.8220 | 2.2 |
| 251 | 2: T20-21 | THTCPPCPAPELLGGPSVFLFPPKPKDTLMISR | 43.45 | 43.69 | 4617.2383 | -1.6 |
| 277 | 2: T22-23 | TPEVTCVVVDVSHEDPEVKFNWYVDGVEVHNAK | 40.62 | 40.76 | 4754.1760 | -2.5 |
| 291 | 2: T23-24 | FNWYVDGVEVHNAKTKPR | 34.86 | 35.23 | 3116.4629 | -2.6 |
| 293 | 2: T24 | TKPR | 34.04 | 34.67 | 1457.6788 | -1.4 |
| 320 | 2: T26-27 | VVSVLTVLHQDWLNGKEYK | 43.49 | 43.77 | 3184.5718 | 0.5 |
| 323 | 2: T27-28 | EYKCK | 33.91 | 34.55 | 1683.7008 | -0.9 |
| 325 | 2: T28-29 | CKVSNK | 33.50 | 34.12 | 1691.7462 | -1.1 |
| 329 | 2: T29-30 | VSNKALPAPIEK | 38.21 | 38.62 | 2223.1061 | -1.6 |
| 337 | 2: T30-31 | ALPAPIEKTISK | 40.26 | 40.64 | 2224.1265 | -1.6 |
| 341 | 2: T31-32 | TISKAK | 34.94 | 35.35 | 1603.7731 | -0.3 |
| 343 | 2: T32-33 | AKGQPR | 33.84 | 34.49 | 1612.7483 | -0.1 |
| 363 | 2: T35-36 | EEMTKNQVSLTCLVK | 40.20 | 40.62 | 2736.2624 | 4.0 |
| 395 | 2: T37-38 | GFYPSDIAVEWESNGQPENNYKTTPPVLDSDGSFFLYSK | 44.37 | 44.71 | 5355.3998 | -1.1 |
| 417 | 2: T39-40 | LTVDKSR | 36.07 | 36.63 | 1774.8375 | -0.9 |
| 442 | 2: T41-42 | WQQGNVFSCSVMHEALHNHYTQKSLSLSPG | 36.81 | 37.06 | 4398.9700 | -2.2 |

*conjugation of DM1 is located on the N-terminal amine group.

TABLE 2

Summary table of linker-only sites identified in T-DM1. The innovator and the candidate biosimilar show the same linker-only sites.

| Unreacted linker conjugated Lys Site | Trypsin Digest | | | | Asp-N Digest | | | |
|---|---|---|---|---|---|---|---|---|
| | Peptide | mass (Da) | RT (min) | Mass error (ppm) | Peptide | mass (Da) | RT (min) | Mass error (ppm) |
| HC136 | 2:T13-14 | 2708.3964 | 29.40 29.52 | −1.8 | Not observed | | | |
| HC213 | 2:T15-16 | 7274.5943 | 37.55 37.68 | 2.0 | 2:D8 | 7031.4724 | 38.76 38.95 | 2.3 |
| HC225 | 2:T19-20 | 3553.7317 | 30.87 31.43 | 0.3 | 2:D10 | 3306.6690 | 31.65 32.23 | 1.0 |

REFERENCES

1. Weiner, L. M., Building better magic bullets—improving unconjugated monoclonal antibody therapy for cancer. *Nature Reviews Cancer* 2007, 7 (9), 701-706.
2. Lambert, J. M., Drug-conjugated monoclonal antibodies for the treatment of cancer. *Current Opinion in Pharmacology* 2005, 5 (5), 543-549.
3. Lewis Phillips, G. D.; Li, G.; Dugger, D. L.; Crocker, L. M.; Parsons, K. L.; Mai, E.; Blattler, W. A.; Lambert, J. M.; Chari, R. V. J.; Lutz, R. J.; Wong, W. L. T.; Jacobson, F. S.; Koeppen, H.; Schwall, R. H.; Kenkare-Mitra, S. R.; Spencer, S. D.; Sliwkowski, M. X., Targeting HER2-positive breast cancer with trastuzumab-DM1, an antibody-cytotoxic drug conjugate. *Cancer Research* 2008, 68 (22), 9280-9290.
4. Kim, M. T.; Chen, Y.; Marhoul, J.; Jacobson, F., Statistical modeling of the drug load distribution on trastuzumab emtansine (Kadcyla), a lysine-linked antibody drug conjugate. *Bioconjugate Chemistry* 2014, 25 (7), 1223-1232.
5. Jung, S. K.; Lee, K. H.; Jeon, J. W.; Lee, J. W.; Kwon, B. O.; Kim, Y. J.; Bae, J. S.; Kim, D.-I.; Lee, S. Y.; Chang, S. J., Physicochemical characterization of Remsima. *mAbs* 2014, 6 (5), 1163-1177.
6. Strop, P.; Liu, S.-H.; Dorywalska, M.; Delaria, K.; Dushin, Russell G.; Tran, T.-T.; Ho, W.-H.; Farias, S.; Casas, Meritxell G.; Abdiche, Y.; Zhou, D.; Chandrasekaran, R.; Samain, C.; Loo, C.; Rossi, A.; Rickert, M.; Krimm, S.; Wong, T.; Chin, Sherman M.; Yu, J.; Dilley, J.; Chaparro-Riggers, J.; Filzen, Gary F.; O'Donnell, Christopher J.; Wang, F.; Myers, Jeremy S.; Pons, J.; Shelton, David L.; Rajpal, A., Location Matters: Site of Conjugation Modulates Stability and Pharmacokinetics of Antibody Drug Conjugates. *Chemistry & Biology* 2013, 20 (2), 161-167.
7. Ionescu, R. M.; Vlasak, J.; Price, C.; Kirchmeier, M., Contribution of variable domains to the stability of humanized IgG1 monoclonal antibodies. *Journal of Pharmaceutical Sciences* 2008, 97 (4), 1414-1426.
8. Wakankar, A. A.; Feeney, M. B.; Rivera, J.; Chen, Y.; Kim, M.; Sharma, V. K.; Wang, Y. J., Physicochemical Stability of the Antibody—Drug Conjugate Trastuzumab-DM1: Changes due to Modification and Conjugation Processes. *Bioconjugate Chemistry* 2010, 21 (9), 1588-1595.
9. Lazar, A. C.; Wang, L.; Blättler, W. A.; Amphlett, G.; Lambert, J. M.; Zhang, W., Analysis of the composition of immunoconjugates using size-exclusion chromatography coupled to mass spectrometry. *Rapid Communications in Mass Spectrometry* 2005, 19 (13), 1806-1814.
10. Xie, H.; Chakraborty, A.; Ahn, J.; Yu, Y. Q.; Dakshinamoorthy, D. P.; Gilar, M.; Chen, W.; Skilton, S. J.; Mazzeo, J. R., Rapid comparison of a candidate biosimilar to an innovator monoclonal antibody with advanced liquid chromatography and mass spectrometry technologies. *MAbs* 2010, 2 (4), 379-94.
11. Zhang, Z., Large-scale identification and quantification of covalent modifications in therapeutic proteins. *Analytical Chemistry* 2009, 81 (20), 8354-8364.
12. Wang, L.; Amphlett, G.; Blättler, W. A.; Lambert, J. M.; Zhang, W., Structural characterization of the maytansinoid-monoclonal antibody immunoconjugate, huN901-DM1, by mass spectrometry. Protein Science: *A Publication of the Protein Society* 2005, 14 (9), 2436-2446.
13. Leavell, M. D.; Novak, P.; Behrens, C. R.; Schoeniger, J. S.; Kruppa, G. H., Strategy for selective chemical cross-linking of tyrosine and lysine residues. *J Am Soc Mass Spectrom* 2004, 15 (11), 1604-11.
14. Duddu, S. P.; Dal Monte, P. R., Effect of glass transition temperature on the stability of lyophilized formulations containing a chimeric therapeutic monoclonal antibody. *Pharm Res* 1997, 14 (5), 591-5.
15. Liu, H.; Bulseco, G. G.; Sun, J., Effect of posttranslational modifications on the thermal stability of a recombinant monoclonal antibody. *Immunol Lett* 2006, 106 (2), 144-53.
16. Ejima, D.; Tsumoto, K.; Fukada, H.; Yumioka, R.; Nagase, K.; Arakawa, T.; Philo, J. S., Effects of acid exposure on the conformation, stability, and aggregation of monoclonal antibodies. *Proteins* 2007, 66 (4), 954-62.

We claim:

1. A method for analyzing site occupancy ratios in antibody-drug conjugates, said method comprising:
   (i) providing a sample comprising an antibody-drug conjugate compound;
   (ii) exposing the sample to de-salting;
   (iii) exposing the sample to multienzyme digestion to form a digested peptide mixture, wherein the digested peptide mixture comprises conjugated peptide and unconjugated peptide;
   (iv) ionizing the sample to form radical ion fragments;
   (v) detecting the mass-to-charge ratios associated with the radical ion fragments;
   (vi) analyzing the mass-to-charge ratios of the radical ion fragments; and
   (vii) quantifying the site occupancy ratio in the sample by determining the ratio of conjugated peptide to conjugated peptide and unconjugated peptide, thereby analyzing site occupancy ratios in antibody-drug conjugates.

2. The method of claim 1, further comprising identifying the conjugated peptide and unconjugated peptide in the sample.

3. The method of claim 1, further comprising selecting two separate groups of mass-to-charge ratios of the radical ion fragments.

4. The method of claim 3, wherein the first group of mass-to-charge ratios is associated with the radical ion fragments of the conjugated peptide.

5. The method of claim 3, wherein the second group of mass-to-charge ratios is associated with the radical ion fragments of the unconjugated peptide.

6. The method of claim 3, wherein the selection of the two separate groups of mass-to-charge ratios is based on known ion fragmentation patterns.

7. The method of claim 6, wherein the known ion fragmentation patterns are stored in a library.

8. The method of claim 1, wherein the multienzyme digestion comprises a first enzyme and a second enzyme.

9. The method of claim 8, wherein the first enzyme is trypsin/Lys C.

10. The method of claim 9, wherein the ratio of the trypsin/Lys C to sample is about 1:25 (w/w).

11. The method of claim 8, wherein the second enzyme is Asp N.

12. The method of claim 11, wherein the ratio of the Asp N to sample is about 1:100 (w/w).

\* \* \* \* \*

SEQUENCE LISTING

<160> NUMBER OF SEQ ID NOS: 43

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

```
Tyr Gly Gly Phe Leu
1               5

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Ser Val Lys Gly Arg Phe Thr Ile Ser Ala
1               5                   10

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Ile Gln Met Thr Gln Ser Pro Ser Ser Leu Ser Ala Ser Val Gly
1               5                   10                  15

Asp Arg

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Ser Gln Asp Val Asn Thr Ala Val Ala Trp Tyr Gln Gln Lys Pro
1               5                   10                  15

Gly Lys Ala Pro Lys
            20

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Pro Lys Leu Leu Ile Tyr Ser Ala Ser Phe Leu Tyr Ser Gly Val
1               5                   10                  15

Pro Ser Arg

<210> SEQ ID NO 6
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ser Gly Thr Asp Phe Thr Leu Thr Ile Ser Ser Leu Gln Pro Glu Asp
```

```
                1               5                  10                  15
Phe Ala Thr Tyr Tyr Cys Gln Gln His Tyr Thr Thr Pro Pro Thr Phe
                20                  25                  30

Gly Gln Gly Thr Lys Val Glu Ile Lys
        35                  40
```

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

```
Val Glu Ile Lys Arg
1               5
```

<210> SEQ ID NO 8
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Thr Val Ala Ala Pro Ser Val Phe Ile Phe Pro Pro Ser Asp Glu Gln
1               5                  10                  15

Leu Lys Ser Gly Thr Ala Ser Val Val Cys Leu Leu Asn Asn Phe Tyr
                20                  25                  30

Pro Arg
```

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

```
Glu Ala Lys Val Gln Trp Lys
1               5
```

<210> SEQ ID NO 10
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

```
Val Gln Trp Lys Val Asp Asn Ala Leu Gln Ser Gly Asn Ser Gln Glu
1               5                  10                  15

Ser Val Thr Glu Gln Asp Ser Lys
            20
```

<210> SEQ ID NO 11
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

Val Asp Asn Ala Leu Gln Ser Gly Asn Ser Gln Glu Ser Val Thr Glu
1               5                   10                  15

Gln Asp Ser Lys Asp Ser Thr Tyr Ser Leu Ser Ser Thr Leu Thr Leu
            20                  25                  30

Ser Lys

<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Ser Thr Tyr Ser Leu Ser Ser Thr Leu Thr Leu Ser Lys Ala Asp
1               5                   10                  15

Tyr Glu Lys

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Asp Tyr Glu Lys His Lys
1               5

<210> SEQ ID NO 14
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

His Lys Val Tyr Ala Cys Glu Val Thr His Gln Gly Leu Ser Ser Pro
1               5                   10                  15

Val Thr Lys

<210> SEQ ID NO 15
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Val Tyr Ala Cys Glu Val Thr His Gln Gly Leu Ser Ser Pro Val Thr
1               5                   10                  15

Lys Ser Phe Asn Arg
            20

<210> SEQ ID NO 16
<211> LENGTH: 19
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 16

Glu Val Gln Leu Val Glu Ser Gly Gly Gly Leu Val Gln Pro Gly Gly
1               5                   10                  15

Ser Leu Arg

<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Ser Cys Ala Ala Ser Gly Phe Asn Ile Lys Asp Thr Tyr Ile His
1               5                   10                  15

Trp Val Arg

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Ala Pro Gly Lys Gly Leu Glu Trp Val Ala Arg
1               5                   10

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Tyr Ala Asp Ser Val Lys Gly Arg
1               5

<210> SEQ ID NO 20
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Phe Thr Ile Ser Ala Asp Thr Ser Lys Asn Thr Ala Tyr Leu Gln Met
1               5                   10                  15

Asn Ser Leu Arg
            20

<210> SEQ ID NO 21
<211> LENGTH: 38
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 21

Trp Gly Gly Asp Gly Phe Tyr Ala Met Asp Tyr Trp Gly Gln Gly Thr
1               5                   10                  15

Leu Val Thr Val Ser Ser Ala Ser Thr Lys Gly Pro Ser Val Phe Pro
            20                  25                  30

Leu Ala Pro Ser Ser Lys
        35

<210> SEQ ID NO 22
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Pro Ser Val Phe Pro Leu Ala Pro Ser Ser Lys Ser Thr Ser Gly
1               5                   10                  15

Gly Thr Ala Ala Leu Gly Cys Leu Val Lys
            20                  25

<210> SEQ ID NO 23
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Tyr Phe Pro Glu Pro Val Thr Val Ser Trp Asn Ser Gly Ala Leu
1               5                   10                  15

Thr Ser Gly Val His Thr Phe Pro Ala Val Leu Gln Ser Ser Gly Leu
            20                  25                  30

Tyr Ser Leu Ser Ser Val Val Thr Val Pro Ser Ser Ser Leu Gly Thr
        35                  40                  45

Gln Thr Tyr Ile Cys Asn Val Asn His Lys Pro Ser Asn Thr Lys
    50                  55                  60

<210> SEQ ID NO 24
<211> LENGTH: 66
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Tyr Phe Pro Glu Pro Val Thr Val Ser Trp Asn Ser Gly Ala Leu
1               5                   10                  15

Thr Ser Gly Val His Thr Phe Pro Ala Val Leu Gln Ser Ser Gly Leu
            20                  25                  30

Tyr Ser Leu Ser Ser Val Val Thr Val Pro Ser Ser Ser Leu Gly Thr
        35                  40                  45

Gln Thr Tyr Ile Cys Asn Val Asn His Lys Pro Ser Asn Thr Lys Val
    50                  55                  60

Asp Lys
65

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Val Asp Lys Lys
1

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Lys Val Glu Pro Lys
1               5

<210> SEQ ID NO 27
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ser Cys Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys
            20                  25                  30

<210> SEQ ID NO 28
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr His Thr Cys Pro Pro Cys Pro Ala Pro Glu Leu Leu Gly Gly Pro
1               5                   10                  15

Ser Val Phe Leu Phe Pro Pro Lys Pro Lys
            20                  25

<210> SEQ ID NO 29
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg

```
<210> SEQ ID NO 30
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30
```

Thr Pro Glu Val Thr Cys Val Val Val Asp Val Ser His Glu Asp Pro
1               5                   10                  15

Glu Val Lys Phe Asn Trp Tyr Val Asp Gly Val Glu Val His Asn Ala
            20                  25                  30

Lys

```
<210> SEQ ID NO 31
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31
```

Phe Asn Trp Tyr Val Asp Gly Val Glu Val His Asn Ala Lys Thr Lys
1               5                   10                  15

Pro Arg

```
<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32
```

Thr Lys Pro Arg
1

```
<210> SEQ ID NO 33
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33
```

Val Val Ser Val Leu Thr Val Leu His Gln Asp Trp Leu Asn Gly Lys
1               5                   10                  15

Glu Tyr Lys

```
<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34
```

```
Glu Tyr Lys Cys Lys
1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Cys Lys Val Ser Asn Lys
1               5

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Val Ser Asn Lys Ala Leu Pro Ala Pro Ile Glu Lys
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ala Leu Pro Ala Pro Ile Glu Lys Thr Ile Ser Lys
1               5                   10

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Thr Ile Ser Lys Ala Lys
1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Lys Gly Gln Pro Arg
1               5

<210> SEQ ID NO 40
<211> LENGTH: 15
<212> TYPE: PRT
<213> ORGANISM: Artificial Sequence
<220> FEATURE:
```

-continued

```
<223> OTHER INFORMATION: Description of Artificial Sequence: Synthetic
      peptide

<400> SEQUENCE: 40

Glu Glu Met Thr Lys Asn Gln Val Ser Leu Thr Cys Leu Val Lys
1               5                   10                  15

<210> SEQ ID NO 41
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gly Phe Tyr Pro Ser Asp Ile Ala Val Glu Trp Glu Ser Asn Gly Gln
1               5                   10                  15

Pro Glu Asn Asn Tyr Lys Thr Thr Pro Pro Val Leu Asp Ser Asp Gly
            20                  25                  30

Ser Phe Phe Leu Tyr Ser Lys
        35

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Leu Thr Val Asp Lys Ser Arg
1               5

<210> SEQ ID NO 43
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Trp Gln Gln Gly Asn Val Phe Ser Cys Ser Val Met His Glu Ala Leu
1               5                   10                  15

His Asn His Tyr Thr Gln Lys Ser Leu Ser Leu Ser Pro Gly
            20                  25                  30
```